United States Patent
Mengiste et al.

(10) Patent No.: US 7,230,159 B2
(45) Date of Patent: Jun. 12, 2007

(54) **ISOLATED BOS1 GENE PROMOTERS FROM *ARABIDOPSIS* AND USES THEREOF**

(75) Inventors: Tesfaye Mengiste, West Lafayette, IN (US); Xi Chen, Research Triangle Park, NC (US); John Salmeron, Research Triangle Park, NC (US); Robert Dietrich, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 195 days.

(21) Appl. No.: 10/505,744

(22) PCT Filed: Mar. 5, 2003

(86) PCT No.: PCT/US03/07331

§ 371 (c)(1),
(2), (4) Date: Jan. 14, 2005

(87) PCT Pub. No.: WO03/076597

PCT Pub. Date: Sep. 18, 2003

(65) Prior Publication Data

US 2005/0120410 A1    Jun. 2, 2005

Related U.S. Application Data

(60) Provisional application No. 60/361,861, filed on Mar. 5, 2002.

(51) Int. Cl.
*C12N 15/82* (2006.01)
*C12N 15/09* (2006.01)
*A01H 5/00* (2006.01)

(52) U.S. Cl. .............. 800/279; 800/278; 800/298; 536/24.1; 435/320.1; 435/468

(58) Field of Classification Search ............. 800/287
See application file for complete search history.

(56) References Cited

U.S. PATENT DOCUMENTS 5,187,267 A * 2/1993 Comai et al. ............ 800/298
6,627,793 B2 * 9/2003 Sarhan et al. ........... 800/278

* cited by examiner

*Primary Examiner*—Medina A. Ibrahim
(74) *Attorney, Agent, or Firm*—Gregory W. Warren

(57) ABSTRACT

The present invention pertains to an isolated promoter sequence from *Arabidopisis thaliana* BOSI gene encoding a protein for biotic and abiotic stress tolerance. Also, the invention relates to recombinant vectors, expression cassettes, host cells, plants or progeny thereof comprising nucleic acid molecules operably linked to said promoter.

8 Claims, 9 Drawing Sheets

- *Alternaria brassicicola*, $10^5$ spores/ml
- 5 dpi

ISOLATED BOS1 GENE PROMOTERS FROM *ARABIDOPSIS* AND USES THEREOF

This application is a § 371 of International Application No. PCT/US03/07331, filed Mar. 5, 2003, which claims the benefit of U.S. Provisional Patent Application No. 60/361,861 filed Mar. 5, 2002, which is incorporated herein by reference.

FIELD OF THE INVENTION

The present invention pertains to nucleic acid molecules isolated from *Arabidopsis thaliana* comprising nucleotide sequences that encode proteins for biotic and abiotic stress tolerance. The invention particularly relates to methods of using nucleic acid molecules and/or proteins from *Arabidopsis* in transgenic plants to confer enhanced biotic and/or abiotic stress tolerance, and to use such nucleic acids to assist germplasm enhancement by breeding. In particular, the invention pertains to nucleic acid molecules isolated from *Arabidopsis thaliana* of the BOS1 cDNA and genomic gene and encoding the BOS1 polypeptide. The present invention also pertains to nucleic acid molecules isolated from *Arabidopsis thaliana* that encode a promoter from the BOS1 gene, and methods of using the promoter. Also, the invention relates to host cells, plants or progeny thereof comprising the nucleic acid molecules or recombinant molecules described herein.

BACKGROUND OF THE INVENTION

Improvement of the agronomic characteristics of crop plants has been ongoing since the beginning of agriculture. Most of the land suitable for crop production is currently being used. As human populations continue to increase, improved crop varieties will be required to adequately provide our food and feed (Trewavas (2001) Plant Physiol. 125: 174–179). To avoid catastrophic famines and malnutrition, future crop cultivars will need to have improved yields with equivalent farm inputs. These cultivars will need to more effectively withstand adverse conditions such as drought, soil salinity or disease, which will be especially important as marginal lands are brought into cultivation. Finally, we will need cultivars with altered nutrient composition to enhance human and animal nutrition, and to enable more efficient food and feed processing, by designing cultivars for specific end-uses. For all these traits, identification of the genes controlling phenotypic expression of traits of interest will be crucial in accelerating development of superior crop germplasm by conventional or transgenic means.

A number of highly efficient approaches are available to assist identification of genes playing key roles in expression of agronomically important traits. These include genetics, genomics, bioinformatics, and functional genomics. Genetics is the scientific study of the mechanisms of inheritance. By identifying mutations that alter the pathway or response of interest, classical (or forward) genetics can help to identify the genes involved in these pathways or responses. For example, a mutant with enhanced susceptibility to disease may identify an important component of the plant signal transduction pathway leading from pathogen recognition to disease resistance. Genetics is also the central component in improvement of germplasm by breeding. Through molecular and phenotypic analysis of genetic crosses, loci controlling traits of interest can be mapped and followed in subsequent generations. Knowledge of the genes underlying phenotypic variation between crop accessions can enable development of markers that greatly increase efficiency of the germplasm improvement process, as well as open avenues for discovery of additional superior alleles. Genomics is the system-level study of an organism's genome, including genes and corresponding gene products—RNA and proteins. At a first level, genomic approaches have provided large datasets of sequence information from diverse plant species, including full-length and partial cDNA sequences, and the complete genomic sequence of a model plant species, *Arabidopsis thaliana*. Recently, the first draft sequence of a crop plant's genome, that of rice (*Oryza sativa*), has also become available. Availability of whole genome sequence makes possible the development of tools for system-level study of other molecular complements, such as arrays and chips for use in determining the complement of expressed genes in an organism under specific conditions. Such data can be used as a first indication of the potential for certain genes to play key roles in expression of different plant phenotypes. Bioinformatics approaches interface directly with first-level genomic datasets in allowing for processing to uncover sequences of interest by annotative or other means. Using, for example, similarity searches, alignments and phylogenetic analyses, bioinformatics can often identify homologs of a gene product of interest. Very similar homologs (eg. >~90% amino acid identity over the entire length of the protein) are very likely orthologs, i.e. share the same function in different organisms.

Functional genomics can be defined as the assignment of function to genes and their products. Functional genomics draws from genetics, genomics and bioinformatics to derive a path toward identifying genes important in a particular pathway or response of interest. Expression analysis, for example, uses high density DNA microarrays (often derived from genomic-scale organismal sequencing) to monitor the mRNA expression of thousands of genes in a single experiment. Experimental treatments can include those eliciting a response of interest, such as the disease resistance response in plants infected with a pathogen. To give additional examples of the use of microarrays, mRNA expression levels can be monitored in distinct tissues over a developmental time course, or in mutants affected in a response of interest. Proteomics can also help to assign function, by assaying the expression and post-translational modifications of hundreds of proteins in a single experiment. Proteomics approaches are in many cases analogous to the approaches taken for monitoring mRNA expression in microarray experiments. Protein-protein interactions can also help to assign proteins to a given pathway or response, by identifying proteins which interact with known components of the pathway or response. For functional genomics, protein-protein interactions are often studied using large-scale yeast two-hybrid assays. Another approach to assigning gene function is to express the corresponding protein in a heterologous host, for example the bacterium *Escherichia coli*, followed by purification and enzymatic assays.

Ultimately, demonstration of the ability of a gene-of-interest to control a given trait must be derived from experimental testing in plant species of interest. The generation and analysis of plants transgenic for a gene of interest can be used for plant functional genomics, with several advantages. The gene can often be both overexpressed and underexpressed ("knocked out"), thereby increasing the chances of observing a phenotype linking the gene to a pathway or response of interest. Two aspects of transgenic functional genomics help lend a high level of confidence to functional assignment by this approach. First, phenotypic observations are carried out in the context of the living plant. Second, the range of phenotypes observed can be checked and correlated with with observed expression levels of the introduced transgene. Transgenic functional genomics is especially valuable in improved cultivar development. Only genes that function in a pathway or response of interest, and that in addition are able to confer a desired trait-based phenotype, are promoted as candidate genes for crop improvement efforts. In some cases, transgenic lines developed for functional genomics studies can be directly utilized in initial stages of product development.

Another approach towards plant functional genomics involves first identifying plant lines with mutations in specific genes of interest, followed by phenotypic evaluation of the consequences of such gene knockouts on the trait under study. Such an approach reveals genes essential for expression of specific traits.

Genes identified through functional genomics can be directly employed in efforts towards germplasm improvement by transgenic means, as described above, or used to develop markers for identification of tracking of alleles-of-interest in mapping and breeding populations. Knowledge of such genes may also enable construction of superior alleles non-existent in nature, by any of a number of molecular methods.

SUMMARY OF THE INVENTION

This Summary of Invention lists several embodiments of the invention, and in many cases lists variations and permutations of these embodiments. This Summary is merely exemplary of the numerous and varied embodiments. Mention of one or more preferred features of a given embodiment is likewise exemplary. Such embodiment can typically exist with or without the feature(s) mentioned; likewise, those features can be applied to other embodiments of the invention, whether listed in this Summary or not. To avoid excessive repetition, this Summary does not list or suggest all possible combinations of such features.

Embodiments of the present invention provide nucleotide and amino acid sequences known as cDNAs from rice.

Embodiments of the present invention relate to an isolated nucleic acid comprising or consisting of a nucleotide sequence including:
  (a) a nucleotide sequence listed in SEQ ID NO:1, fragment, domain, or feature thereof;
  (b) a nucleotide sequence having substantial similarity to (a);
  (c) a nucleotide sequence capable of hybridizing to (a);
  (d) a nucleotide sequence complementary to (a), (b) or (c); and
  (e) a nucleotide sequence which is the reverse complement of (a), (b) or (c).

In a preferred embodiment, the substantial similarity is at least about 65% identity, preferably about 80% identity, preferably 90%, and more preferably at least about 95% identity to the nucleotide sequence listed in SEQ ID NO:1, fragment, domain, or feature thereof.

In a preferred embodiment, the sequence having substantial similarity to the nucleotide sequence listed in SEQ ID NO:1, fragment, domain, or feature thereof, is from a plant. In a preferred embodiment, the plant is a dicot. In another preferred embodiment, the plant is a gymnosperm. In a more preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum* sp., or teosinte. In a most preferred embodiment, the cereal is rice.

In a preferred embodiment, the nucleic acid is expressed in a specific location or tissue of a plant. In a more preferred embodiment, the location or tissue is for example, but not limited to, epidermis, root, vascular tissue, meristem, cambium, cortex, pith, leaf, and flower. In a most preferred embodiment, the location or tissue is a seed. In another preferred embodiment, the nucleic acid encodes a polypeptide involved in a function such as, for example, but not limited to, carbon metabolism, photosynthesis, signal transduction, cell growth, reproduction, disease processes, gene regulation, and differentiation. In a more preferred embodiment, the nucleic acid encodes a polypeptide involved in abiotic stress tolerance, enhanced yield, disease resistance, or nutritional content.

In a preferred embodiment, the isolated nucleic acid comprising or consisting of a nucleotide sequence capable of hybridizing to a nucleotide sequence listed in SEQ ID No:1, or fragment, domain, or feature thereof. In a preferred embodiment, hybridization allows the sequence to form a duplex atmedium or high stringency. Embodiments of the present invention also encompass a nucleotide sequence complementary to a nucleotide sequence listed in SEQ ID No:1, or fragment, domain, or feature thereof. Embodiments of the present invention further encompass a nucleotide sequence complementary to a nucleotide sequence that has substantial similarity or is capable of hybridizing to a nucleotide sequence listed in SEQ ID No:1, or fragment, domain, or feature thereof.

In a preferred embodiment, the nucleotide sequence having substantial similarity is an allelic variant of the nucleotide sequence listed in SEQ ID No:1, or fragment, domain, or feature thereof. In an alternate embodiment, the sequence having substantial similarity is a naturally occurring variant. In another alternate embodiment, the sequence having substantial similarity is a polymorphic variant of the nucleotide sequence listed in SEQ ID No:1, or fragment, domain, or feature thereof.

In a preferred embodiment, the isolated nucleic acid contains a plurality of regions having the nucleotide sequence listed in SEQ ID NO:1, or exon, domain, or feature thereof.

In a preferred embodiment, the isolated nucleic acid contains a polypeptide-encoding sequence. In a more preferred embodiment, the polypeptide-encoding sequence contains a 20 base pair nucleotide portion identical in sequence to a consecutive 20 base pair nucleotide portion of a nucleic acid sequence listed in SEQ ID NO:1. In a more preferred embodiment, the polypeptide contains a polypeptide sequence listed in SEQ ID No:2, or a fragment thereof. In a more preferred embodiment, the polypeptide is a plant polypeptide. In a more preferred embodiment, the plant is a dicot. In a more preferred embodiment, the plant is a gymnosperm. In a more preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, miloflax, gramma grass, *Tripsacum,* and teosinte. In a most preferred embodiment, the cereal is rice.

In one embodiment, the polypeptide is expressed throughout the plant. In a more preferred embodiment, the polypeptide is expressed in a specific location or tissue of a plant. In a more preferred embodiment, the location or tissue may be, for example, epidermis, root, vascular tissue, meristem, cambium, cortex, pith, leaf, and flower. In a most preferred embodiment, the location or tissue is a seed.

In a preferred embodiment, the polypeptide is involved in a function such as abiotic stress tolerance, enhanced yield, disease resistance or nutritional content.

In a preferred embodiment, the sequence of the isolated nucleic acid encodes a polypeptide useful for generating an antibody having immunoreactivity against a polypeptide encoded by a nucleotide sequence listed in SEQ ID No:2, or fragment, domain, or feature thereof.

In a preferred embodiment, the sequence having substantial similarity contains a deletion or insertion of at least one nucleotide. In a more preferred embodiment, the deletion or insertion is of less than about thirty nucleotides. In a most preferred embodiment, the deletion or insertion is of less than about five nucleotides.

In a preferred embodiment, the sequence of the isolated nucleic acid having substantial similarity comprises or consists of a substitution in at least one codon. In a preferred embodiment, the substitution is conservative.

Embodiments of the present invention also relate to the an isolated nucleic acid molecule comprising or consisting of a nucleotide sequence, its complement, or its reverse complement, encoding a polypeptide including:
   (a) a polypeptide sequence listed in SEQ ID No:2, or a fragment, domain, repeat, feature, or chimera thereof;
   (b) a polypeptide sequence having substantial similarity to (a);
   (c) a polypeptide sequence encoded by a nucleotide sequence identical to or having substantial similarity to a nucleotide sequence listed in SEQ ID No:1, or a fragment, domain, or feature thereof, or a sequence complementary thereto;
   (d) a polypeptide sequence encoded by a nucleotide sequence capable of hybridizing under medium stringency conditions to a nucleotide sequence listed in SEQ ID No:1, or to a sequence complementary thereto; and
   (e) a functional fragment of (a), (b), (c) or (d).

In another preferred embodiment, the polypeptide having substantial similarity is an allelic variant of a polypeptide sequence listed in SEQ ID NO:2, or a fragment, domain, repeat, feature, or chimeras thereof. In another preferred embodiment, the isolated nucleic acid includes a plurality of regions from the polypeptide sequence encoded by a nucleotide sequence identical to or having substantial similarity to a nucleotide sequence listed in SEQ ID NO:1, or fragment, domain, or feature thereof, or a sequence complementary thereto.

In another preferred embodiment, the polypeptide is a polypeptide sequence listed in SEQ ID NO:2. In another preferred embodiment, the polypeptide is a functional fragment or domain. In yet another preferred embodiment, the polypeptide is a chimera, where the chimera may include functional protein domains, including domains, repeats, post-translational modification sites, or other features. In a more preferred embodiment, the polypeptide is a plant polypeptide. In a more preferred embodiment, the plant is a dicot. In a more preferred embodiment, the plant is a gymnosperm. In a more preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum,* and teosinte. In a most preferred embodiment, the cereal is rice.

In a preferred embodiment, the polypeptide is expressed in a specific location or tissue of a plant. In a more preferred embodiment, the location or tissue may be, for example, epidermis, root, vascular tissue, meristem, cambium, cortex, pith, leaf, and flower. In a more preferred embodiment, the location or tissue is a seed.

In a preferred embodiment, the polypeptide is involved in a function such as abiotic stress tolerance, disease resistance, enhanced yield or nutritional quality or composition.

In a preferred embodiment, the polypeptide sequence encoded by a nucleotide sequence having substantial similarity to a nucleotide sequence listed in SEQ ID No:1 or a fragment, domain, or feature thereof or a sequence complementary thereto, includes a deletion or insertion of at least one nucleotide. In a more preferred embodiment, the deletion or insertion is of less than about thirty nucleotides. In a most preferred embodiment, the deletion or insertion is of less than about five nucleotides.

In a preferred embodiment, the polypeptide sequence encoded by a nucleotide sequence having substantial similarity to a nucleotide sequence listed in SEQ ID No:1, or fragment, domain, or feature thereof or a sequence complementary thereto, includes a substitution of at least one codon. In a more preferred embodiment, the substitution is conservative.

In a preferred embodiment, the polypeptide sequences having substantial similarity to the polypeptide sequence listed in SEQ ID No:2, or a fragment, domain, repeat, feature, or chimeras thereof includes a deletion or insertion of at least one amino acid.

In a preferred embodiment, the polypeptide sequences having substantial similarity to the polypeptide sequence listed in SEQ ID No:2, or a fragment, domain, repeat, feature, or chimeras thereof includes a substitution of at least one amino acid.

Embodiments of the present invention also relate to a shuffled nucleic acid containing a plurality of nucleotide sequence fragments, wherein at least one of the fragments corresponds to a region of a nucleotide sequence listed in SEQ ID NO:1, and wherein at least two of the plurality of sequence fragments are in an order, from 5' to 3' which is not an order in which the plurality of fragments naturally occur in a nucleic acid. In a more preferred embodiment, all of the fragments in a shuffled nucleic acid containing a plurality of nucleotide sequence fragments are from a single gene. In a more preferred embodiment, the plurality of fragments originates from at least two different genes. In a more preferred embodiment, the shuffled nucleic acid is operably linked to a promoter sequence. Another more preferred embodiment is a chimeric polynucleotide including a promoter sequence operably linked to the shuffled nucleic acid. In a more preferred embodiment, the shuffled nucleic acid is contained within a host cell.

Embodiments of the present invention also contemplate an expression cassette including a promoter sequence operably linked to an isolated nucleic acid containing a nucleotide sequence including:
   (a) a nucleotide sequence listed in SEQ ID NO:1, or fragment, domain, or feature thereof;
   (b) a nucleotide sequence having substantial similarity to (a);
   (c) a nucleotide sequence capable of hybridizing to (a);
   (d) a nucleotide sequence complementary to (a), (b) or (c); and
   (e) a nucleotide sequence which is the reverse complement of (a), (b) or (c).

Further encompassed within the invention, is a recombinant vector comprising an expression cassette according to embodiments of the present invention. Also encompassed are plant cells, which contain expression cassettes, according to the present disclosure, and plants, containing these plant cells. In a preferred embodiment, the plant is a dicot. In another preferred embodiment, the plant is a gymnosperm. In another preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum* and teosinte. In a most preferred embodiment, the cereal is rice.

In one embodiment, the expression cassette is expressed throughout the plant. In another embodiment, the expression cassette is expressed in a specific location or tissue of a plant. In a preferred embodiment, the location or tissue may be, for example, epidermis, root, vascular tissue, meristem, cambium, cortex, pith, leaf, and flower. In a more preferred embodiment, the location or tissue is a seed.

In one embodiment, the expression cassette is involved in a function such as, for example, but not limited to, disease resistance, yield, abiotic stress resistance, nutritional quality, carbon metabolism, photosynthesis, signal transduction, cell growth, reproduction, disease processes, gene regulation, and differentiation. In a more preferred embodiment, the chimeric polypeptide is involved in a function such as, abiotic stress tolerance, enhanced yield, disease resistance or nutritional composition.

In one embodiment, the plant contains a modification to a phenotype or measurable characteristic of the plant, the modification being attributable to theexpression cassette. In a preferred embodiment, the modification may be, for example, nutritional enhancement, increased nutrient uptake efficiency, enhanced production of endogenous compounds, and production of heterologous compounds. In another preferred embodiment, the modification includes having increased or decreased resistance to an herbicide, a stress, or a pathogen. In another preferred embodiment, the modification includes having enhanced or diminished requirement for light, water, nitrogen, or trace elements. In another preferred embodiment, the modification includes being enriched for an essential amino acid as a proportion of a protein fraction of the plant. In a more preferred embodiment, the protein fraction may be, for example, total seed protein, soluble protein, insoluble protein, water-extractable protein, and lipid-associated protein. In another preferred embodiment, the modification includes overexpression, underexpression, antisense modulation, sense suppression, inducible expression, inducible repression, or inducible modulation of a gene.

Embodiments of the present invention also provide seed and isolated product from plants which contain an expression cassette including a promoter sequence operably linked to an isolated nucleic acid containing a nucleotide sequence including:
(a) a nucleotide sequence listed in SEQ ID NO:1, or fragment, domain, or feature thereof;
(b) a nucleotide sequence encoding a polypeptide of SEQ ID NO:2, fragment, domain or feature thereof;
(c) a nucleotide sequence having substantial similarity to (a) or (b);
(d) a nucleotide sequence capable of hybridizing to (a), (b) or (c);
(e) a nucleotide sequence complementary to (a), (b), (c) or (d); and
(f) a nucleotide sequence that is the reverse complement of (a), (b), (c) or (d) according to the present disclosure.

Embodiments of the present invention also relate to isolated products produced by expression of an isolated nucleic acid containing a nucleotide sequence including:
(a) a nucleotide sequence listed in SEQ ID NO:1, or fragment, domain, or feature thereof;
(b) a nucleotide sequence encoding a polypeptide listed in SEQ ID NO: 2, or fragment, domain or feature thereof;
(c) a nucleotide sequence having substantial similarity to (a) or (b);
(d) a nucleotide sequence capable of hybridizing to (a) or (b);
(e) a nucleotide sequence complementary to (a), (b), (c) or (d); and
(f) a nucleotide sequence that is the reverse complement of (a), (b) (c) or (d) according to the present disclosure.

In a preferred embodiment, the product is produced in a plant. In another preferred embodiment, the product is produced in cell culture. In another preferred embodiment, the product is produced in a cell-free system. In another preferred embodiment, the product includes an enzyme, a nutritional protein, a structural protein, an amino acid, a lipid, a fatty acid, a polysaccharide, a sugar, an alcohol, an alkaloid, a carotenoid, a propanoid, a steroid, a pigment, a vitamin and a plant hormone.

In a preferred embodiment, the product is a polypeptide containing an amino acid sequence listed in SEQ ID NO:2. In a more preferred embodiment, the protein is an enzyme.

Embodiments of the present invention further relate to an isolated polynucleotide including a nucleotide sequence of at least 10 bases, which sequence is identical, complementary, or substantially similar to a region of any sequence of SEQ ID NO:1, and wherein the polynucleotide is adapted for any of numerous uses.

In a preferred embodiment, the polynucleotide is used as a chromosomal marker. In another preferred embodiment, the polynucleotide is used as a marker for RFLP analysis. In another preferred embodiment, the polynucleotide is used as a marker for quantitative trait linked breeding. In another preferred embodiment, the polynucleotide is used as a marker for marker-assisted breeding. In another preferred embodiment, the polynucleotide is used as a bait sequence in a two-hybrid system to identify sequence-encoding polypeptides interacting with the polypeptide encoded by the bait sequence. In another preferred embodiment, the polynucleotide is used as a diagnostic indicator for genotyping or identifying an individual or population of individuals. In another preferred embodiment, the polynucleotide is used for genetic analysis to identify boundaries of genes or exons.

Embodiments of the present invention also relate to an expression vector comprising or consisting of a nucleic acid molecule including:
(a) a nucleic acid encoding a polypeptide as listed in SEQ ID NO:2;
(b) a fragment, one or more domains, or featured regions listed in SEQ ID NO:1; and
(c) a complete nucleic acid sequence listed in SEQ ID NO:1, or a fragment thereof, in combination with a heterologous sequence.

In a preferred embodiment, the expression vector includes one or more elements such as, for example, but not limited to, a promoter-enhancer sequence, a selection marker sequence, an origin of replication, an epitope-tag encoding sequence, or an affinity purification-tag encoding sequence. In a more preferred embodiment, the promoter-enhancer sequence may be, for example, the CaMV 35S promoter, the CaMV 19S promoter, the tobacco PR-1a promoter, ubiquitin and the phaseolin promoter. In another embodiment, the promoter is operable in plants, and more preferably, a constitutive or inducible promoter. In another preferred embodiment, the selection marker sequence encodes an antibiotic resistance gene. In another preferred embodiment, the epitope-tag sequence encodes V5, the peptide Phe-His-His-Thr-Thr, hemagglutinin, or glutathione-S-transferase. In another preferred embodiment the affinity purification-tag sequence encodes a polyamino acid sequence or a polypeptide. In a more preferred embodiment, the polyamino acid sequence is polyhistidine. In a more preferred embodiment, the polypeptide is chitin binding domain or glutathione-S-transferase. In a more preferred embodiment, the affinity purification-tag sequence comprises an intein encoding sequence.

In a preferred embodiment, the expression vector is a eukaryotic expression vector or a prokaryotic expression vector. In a more preferred embodiment, the eukaryotic expression vector includes a tissue-specific promoter. More preferably, the expression vector is operable in plants.

Embodiments of the present invention also relate to a cell comprising or consisting of a nucleic acid construct comprising an expression vector and a nucleic acid including a nucleic acid encoding a polypeptide as listed in SEQ ID NO:2, or a nucleic acid sequence listed in SEQ ID NO:1, or a segment thereof, in combination with a heterologous sequence.

In a preferred embodiment, the cell is a bacterial cell, a fungal cell, a plant cell, or an animal cell. In a more preferred embodiment, the polypeptide is expressed in a specific location or tissue of a plant. In a most preferred embodiment, the location or tissue may be, for example, epidermis, root, vascular tissue, meristem, cambium, cortex, pith, leaf, and flower. In an alternate most preferred embodiment, the location or tissue is a seed. In a preferred embodiment, the polypeptide is involved in a function such as, for example, carbon metabolism, photosynthesis, signal transduction, cell growth, reproduction, disease processes, gene regulation, and differentiation. More preferably, the polypeptide is involved in a function such as, abiotic stress tolerance, enhanced yield, disease resistance or nutritional composition.

Embodiments of the present invention also relate to polypeptides encoded by the isolated nucleic acid molecules of the present disclosure including a polypeptide containing a polypeptide sequence encoded by an isolated nucleic acid containing a nucleotide sequence including:
 (a) a nucleotide sequence listed in SEQ ID NO:1, or exon, domain, or feature thereof;
 (b) a nucleotide sequence having substantial similarity to (a);
 (c) a nucleotide sequence capable of hybridizing to (a);
 (d) a nucleotide sequence complementary to (a), (b) or (c); and
 (e) a nucleotide sequence which is the reverse complement of (a), (b) or (c);
 (f) or a functional fragment thereof.

A polypeptide containing a polypeptide sequence encoded by an isolated nucleic acid containing a nucleotide sequence, its complement, or its reverse complement, encoding a polypeptide including a polypeptide sequence including:
 (a) a polypeptide sequence listed in SEQ ID NO:2, or a domain, repeat, feature, or chimeras thereof;
 (b) a polypeptide sequence having substantial similarity to (a);
 (c) a polypeptide sequence encoded by a nucleotide sequence identical to or having substantial similarity to a nucleotide sequence listed in SEQ ID NO:1, or an exon, domain, or feature thereof, or a sequence complementary thereto;
 (d) a polypeptide sequence encoded by a nucleotide sequence capable of hybridizing under medium stringency conditions to a nucleotide sequence listed in SEQ ID NO:1, or to a sequence complementary thereto; and
 (e) a functional fragment of (a), (b), (c) or (d);
 (f) or a functional fragment thereof.

Embodiments of the present invention contemplate a polypeptide containing a polypeptide sequence encoded by an isolated nucleic acid which includes a shuffled nucleic acid containing a plurality of nucleotide sequence fragments, wherein at least one of the fragments corresponds to a region of a nucleotide sequence listed in SEQ ID NO:1, and wherein at least two of the plurality of sequence fragments are in an order, from 5' to 3' which is not an order in which the plurality of fragments naturally occur in a nucleic acid, or functional fragment thereof.

Embodiments of the present invention contemplate a polypeptide containing a polypeptide sequence encoded by an isolated polynucleotide containing a nucleotide sequence of at least 10 bases, which sequence is identical, complementary, or substantially similar to a region of any of sequences of SEQ ID NO:1, and wherein the polynucleotide is adapted for a use including:
 (a) use as a chromosomal marker to identify the location of the corresponding or complementary polynucleotide on a native or artificial chromosome;
 (b) use as a marker for RFLP analysis;
 (c) use as a marker for quantitative trait linked breeding;
 (d) use as a marker for marker-assisted breeding;
 (e) use as a bait sequence in a two-hybrid system to identify sequence encoding polypeptides interacting with the polypeptide encoded by the bait sequence;
 (f) use as a diagnostic indicator for genotyping or identifying an individual or population of individuals; and
 (g) use for genetic analysis to identify boundaries of genes or exons;
 (h) or functional fragment thereof.

Embodiments of the present invention also contemplate an isolated polypeptide containing a polypeptide sequence including:
 (a) a polypeptide sequence listed in SEQ ID NO:2, or exon, domain, or feature thereof;
 (b) a polypeptide sequence having substantial similarity to (a);
 (c) a polypeptide sequence encoded by a nucleotide sequence identical to or having substantial similarity to a nucleotide sequence listed in SEQ ID NO:1, or an exon, domain, or feature thereof, or a sequence complementary thereto;
 (d) a polypeptide sequence encoded by a nucleotide sequence capable of hybridizing under medium stringency conditions to a nucleotide sequence listed in SEQ ID NO:1, or to a sequence complementary thereto; and
 (e) a functional fragment of (a), (b), (c) or (d).

In a preferred embodiment, the substantial similarity is at least about 65% identity. In a more preferred embodiment, the substantial similarity is at least about 80% identity. In a most preferred embodiment, the substantial similarity is at least about 95% identity. In a preferred embodiment, the substantial similarity is at least three percent greater than the percent identity to the closest homologous sequence listed in any of the Tables.

In a preferred embodiment, the sequence having substantial similarity is from a plant. In a more preferred embodiment, the plant is a dicot. In a more preferred embodiment, the plant is a gymnosperm. In a more preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum* and teosinte. In a most preferred embodiment, the cereal is rice.

In a preferred embodiment, the polypeptide is expressed in a specific location or tissue of a plant. In a more preferred embodiment, the location or tissue may be, for example, epidermis, root, vascular tissue, meristem, cambium, cortex, pith, leaf, and flower. In a more preferred embodiment, the location or tissue is a seed. In a preferred embodiment, the polypeptide is involved in a function such as, for example, carbon metabolism, photosynthesis, signal transduction, cell growth, reproduction, disease processes, gene regulation, and differentiation.

In a preferred embodiment, hybridization of a polypeptide sequence encoded by a nucleotide sequence identical to or having substantial similarity to a nucleotide sequence listed in SEQ ID NO:1, or an exon, domain, or feature thereof, or a sequence complementary thereto, or a polypeptide sequence encoded by a nucleotide sequence capable of hybridizing under medium stringency conditions to a nucleotide sequence listed in SEQ ID NO:1, or to a sequence complementary thereto, allows the sequence to form a duplex atmedium or high stringency.

In a preferred embodiment, a polypeptide having substantial similarity to a polypeptide sequence listed in SEQ ID NO:2, or exon, domain, or feature thereof, is an allelic variant of the polypeptide sequence listed in SEQ ID NO:2. In another preferred embodiment, a polypeptide having substantial similarity to a polypeptide sequence listed in SEQ ID NO:2, or exon, domain, or feature thereof, is a naturally occurring variant of the polypeptide sequence listed in SEQ ID NO:2. In another preferred embodiment, a polypeptide having substantial similarity to a polypeptide sequence listed in SEQ ID NO:2, or exon, domain, or feature thereof, is a polymorphic variant of the polypeptide sequence listed in SEQ ID NO:2.

In an alternate preferred embodiment, the sequence having substantial similarity contains a deletion or insertion of at least one amino acid. In a more preferred embodiment, the deletion or insertion is of less than about ten amino acids. In a most preferred embodiment, the deletion or insertion is of less than about three amino acids.

In a preferred embodiment, the sequence having substantial similarity encodes a substitution in at least one amino acid.

Also contemplated is a method of producing a plant having enhanced tolerance to biotic and/or abiotic stress comprising the steps of:
  (1) providing a nucleic acid which is an isolated nucleic acid containing a nucleotide sequence including:
    (a) a nucleotide sequence listed in SEQ ID NO:1, or exon, domain, or feature thereof;
    (b) a nucleotide sequence having substantial similarity to (a);
    (c) a nucleotide sequence capable of hybridizing to (a);
    (d) a nucleotide sequence complementary to (a), (b) or (c); and
    (e) a nucleotide sequence which is the reverse complement of (a), (b) or (c);

and (2) introducing the nucleic acid into the plant, wherein the nucleic acid is expressible in the plant in an amount effective to enhance the tolerance to abiotic stress.

Also encompassed within the presently disclosed invention is a method of producing a recombinant protein, comprising the steps of:
  (a) growing recombinant cells comprising a nucleic acid construct Under suitable growth conditions, the construct comprising an expression vector and a nucleic acid including: a nucleic acid encoding a protein as listed in SEQ ID NO:2, or a nucleic acid sequence listed in SEQ ID NOS:1, or segments thereof; and
  (b) isolating from the recombinant cells the recombinant protein expressed thereby.

Embodiments of the present invention provide a method of producing a recombinant protein in which the expression vector includes one or more elements including a promoter-enhancer sequence, a selection marker sequence, an origin of replication, an epitope-tag encoding sequence, and an affinity purification-tag encoding sequence. In one preferred embodiment, the nucleic acid construct includes an epitope-tag encoding sequence and the isolating step includes use of an antibody specific for the epitope-tag. In another preferred embodiment, the nucleic acid construct contains a polyamino acid encoding sequence and the isolating step includes use of a resin comprising a polyamino acid binding substance, preferably where the polyamino acid is polyhistidine and the polyamino binding resin is nickel-charged agarose resin. In yet another preferred embodiment, the nucleic acid construct contains a polypeptide encoding sequence and the isolating step includes the use of a resin containing a polypeptide binding substance, preferably where the polypeptide is a chitin binding domain and the resin contains chitin-sepharose.

Embodiments of the present invention also relate to a plant modified by a method that includes introducing into a plant a nucleic acid where the nucleic acid is expressible in the plant in an amount effective to effect the modification. The modification can be, for example, nutritional enhancement, increased nutrient uptake efficiency, enhanced production of endogenous compounds, and production of heterologous compounds. In one embodiment, the modified plant has increased or decreased resistance to an herbicide, a stress, or a pathogen. In another embodiment, the modified plant has enhanced or diminished requirement for light, water, nitrogen, or trace elements. In yet another embodiment, the modified plant is enriched for an essential amino acid as a proportion of a protein fraction of the plant. The protein fraction may be, for example, total seed protein, soluble protein, insoluble protein, water-extractable protein, and lipid-associated protein. The modification may include overexpression, underexpression, antisense modulation, sense suppression, inducible expression, inducible repression, or inducible modulation of a gene.

The invention further relates to a seed from a modified plant or an isolated product of a modified plant, where the product may be an enzyme, a nutritional protein, a structural protein, an amino acid, a lipid, a fatty acid, a polysaccharide, a sugar, an alcohol, an alkaloid, a carotenoid, a propanoid, a steroid, a pigment, a vitamin and a plant hormone.

The invention further relates to an isolated nucleic acid molecule capable of driving biotic and/or abiotic stress responsive expression of an associated nucleotide sequence in particular, wherein said isolated nucleic acid molecule a) is a component of SEQ ID NO:4;

b) is depicted in SEQ ID NO:4;

c) comprises the nucleotide sequence depicted in SEQ ID NO:4;

d) hybridizes under stringent conditions to SEQ ID NO:4 or SEQ ID NO:3, wherein the nucleic acid molecule is capable of driving stress responsive expression of an associated nucleotide sequence; or e) comprises a consecutive stretch of at least 50 nt, preferably of about 500 bases, particularly of between about 1000 bases and about 1500 bases, and more particularly of about 1551 bases SEQ ID NO:4, wherein said isolated nucleic acid molecule is capable of driving abiotic stress responsive expression of an associated nucleotide sequence, in particular, wherein said consecutive stretch of at least 50 nt has at least 70%, preferably 80%, more preferably 90% and most preferably 95% sequence identity sequence identity with a consecutive stretch of corresponding length of SEQ ID NO:4.

The invention further provides for an isolated nucleic acid molecule comprising the sequence of SEQ ID NO:3 which encodes the genomic clone of the *Arabidopsis thaliana* BOS1 gene.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments that follow.

BRIEF DESCRIPTION OF THE SEQUENCES IN THE SEQUENCE LIST

SEQ ID NO:1 is the cDNA nucleotide sequence of the BOS1 gene from *Arabidopsis thaliana*.

SEQ ID NO:2 is the deduced amino acid sequence of the BOS1 protein encoded by SEQ ID NO:1.

SEQ ID NO:3 is the genomic nucleotide sequence of the BOS1 gene from *Arabidopsis thaliana*.

SEQ ID NO:4 is the nucleotide sequence of the promoter of the BOS1 gene from *Arabidopsis thaliana*.

SEQ ID NO:5 is the 3' RACE primer 1.

SEQ ID NO:6 is the 3'RACE primer 2.

SEQ ID NO:7 is the 5' RACE primer 1.

SEQ ID NO:8 is the 5' RACE primer 2.

SEQ ID NO:9 is the BOS1 cDNA forward primer.

SEQ ID NO:10 is the BOS1 cDNA reverse primer.

SEQ ID NO:11 is the BOS1 genomic forward primer.

SEQ ID NO:12 is the BOS1 genomic reverse primer.

SEQ ID NO:13 is the BOS1 promoter forward primer.

SEQ ID NO:14 is the BOS1 promoter reverse primer.

DEFINITIONS

Figure 1:
FIG. 1 shows a botrytis susceptible (bos1) mutant from a T-DNA mutagenized population based on its increased susceptibility to *Botrytis cinerea* compared to wild type parental ecotype Col-0 plants.
Figure 1:
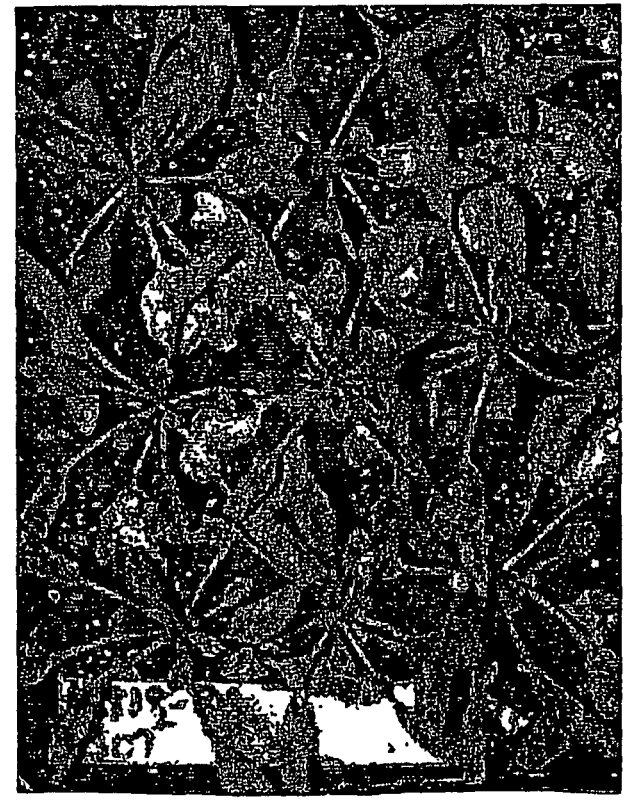

For clarity, certain terms used in the specification are defined and presented as follows:

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric construct" is a recombinant nucleic acid sequence in which a promoter or regulatory nucleic acid sequence is operatively linked to, or associated with, a nucleic acid sequence that codes for an mRNA or which is expressed as a protein, such that the regulatory nucleic acid sequence is able to regulate transcription or expression of the associated nucleic acid sequence. The regulatory nucleic acid sequence of the chimeric construct is not normally operatively linked to the associated nucleic acid sequence as found in nature.

A "co-factor" is a natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosyl-methionine, pyridoxal phosphate, ubiquinone, menaquinone. Optionally, a co-factor can be regenerated and reused.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

Complementary: "complementary" refers to two nucleotide sequences that comprise antiparallel nucleotide sequences capable of pairing with one another upon formation of hydrogen bonds between the complementary base residues in the antiparallel nucleotide sequences.

Enzyme activity: means herein the ability of an enzyme to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Expression Cassette: "Expression cassette" as used herein means a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue or organ or stage of development.

Gene: the term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

Heterologous/exogenous: The terms "heterologous" and "exogenous" when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA) sequence naturally associated with a host cell into which it is introduced.

Hybridization: The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

Inhibitor: a chemical substance that inactivates the enzymatic activity of a protein such as a biosynthetic enzyme, receptor, signal transduction protein, structural gene product, or transport protein. The term "herbicide" (or "herbicidal compound") is used herein to define an inhibitor applied to a plant at any stage of development, whereby the herbicide inhibits the growth of the plant or kills the plant.

Interaction: quality or state of mutual action such that the effectiveness or toxicity of one protein or compound on another protein is inhibitory (antagonists) or enhancing (agonists).

A nucleic acid sequence is "isocoding with" a reference nucleic acid sequence when the nucleic acid sequence encodes a polypeptide having the same amino acid sequence as the polypeptide encoded by the reference nucleic acid sequence.

Isogenic: plants that are genetically identical, except that they may differ by the presence or absence of a heterologous DNA sequence.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

Mature protein: protein from which the transit peptide, signal peptide, and/or propeptide portions have been removed.

Minimal Promoter: the smallest piece of a promoter, such as a TATA element, that can support any transcription. A minimal promoter typically has greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Native: refers to a gene that is present in the genome of an untransformed plant cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

Nucleic acid: the term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J. Biol. Chem.* 260: 2605–2608 (1985); Rossolini et al., *Mol. Cell. Probes* 8: 91–98 (1994)). The terms "nucleic acid" or "nucleic acid sequence" may also be used interchangeably with gene, cDNA, and mRNA encoded by a gene.

"ORF" means open reading frame.

Percent identity: the phrases "percent identical" or "percent identical," in the context of two nucleic acid or protein sequences, refers to two or more sequences or subsequences that have for example 60%, preferably 70%, more preferably 80%, still more preferably 90%, even more preferably 95%, and most preferably at least 99% nucleotide or amino acid residue identity, when compared and aligned for maximum correspondence, as measured using one of the following sequence comparison algorithms or by visual inspection. Preferably, the percent identity exists over a region of the sequences that is at least about 50 residues in length, more preferably over a region of at least about 100 residues, and most preferably the percent identity exists over at least about 150 residues. In an especially preferred embodiment, the percent identity exists over the entire length of the coding regions.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403–410 (1990). Software for performing BLAST analyses is publicly available through the National Center for Biotechnology Information at the World Wide Web site ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always>0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873–5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Pre-protein: protein that is normally targeted to a cellular organelle, such as a chloroplast, and still comprises its native transit peptide.

Promoter: refers to a DNA sequence that initiates transcription of an associated DNA sequence. The promoter region may also include elements that act as regulators of gene expression such as activators, enhancers, and/or repressors and may include all or part of the 5' non-translated region.

Purified: the term "purified," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

"Regulatory elements" refer to sequences involved in controlling the expression of a nucleotide sequence. Regulatory elements comprise a promoter operatively linked to the nucleotide sequence of interest and termination signals. They also typically encompass sequences required for proper translation of the nucleotide sequence.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is reduced by more than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

Specific Binding/Immunological Cross-Reactivity: An indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions. The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A "subsequence" refers to a sequence of nucleic acids or amino acids that comprise a part of a longer sequence of nucleic acids or amino acids (e.g., protein) respectively.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Transformation: a process for introducing heterologous DNA into a plant cell, plant tissue, or plant. Transformed plant cells, plant tissue, or plants are understood to encompass not only the end product of a transformation process, but also transgenic progeny thereof.

"Transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

Viability: "viability" as used herein refers to a fitness parameter of a plant. Plants are assayed for their homozygous performance of plant development, indicating which proteins are essential for plant growth.

DETAILED DESCRIPTION OF THE INVENTION

I. General Description of Trait Functional Genomics Project

The goal of functional genomics is to identify genes controlling expression of organismal phenotypes, and employs a variety of methodologies, including but not limited to bioinformatics, gene expression studies, gene and gene product interactions, genetics, biochemistry and molecular genetics. For example, bioinformatics can assign function to a given gene by identifying genes in heterologous organisms with a high degree of similarity (homology) at the amino acid or nucleotide level. Expression of a gene at the mRNA or protein levels can assign function by linking expression of a gene to an environmental response, a developmental process or a genetic (mutational) or molecular genetic (gene overexpression or underexpression) perturbation. Expression of a gene at the mRNA level can be ascertained either alone (Northern analysis) or in concert with other genes (microarray analysis), whereas expression of a gene at the protein level can be ascertained either alone (native or denatured protein gel or immunoblot analysis) or in concert with other genes (proteomic analysis). Knowledge of protein/protein and protein/DNA interactions can assign function by identifying proteins and nucleic acid sequences acting together in the same biological process. Genetics can assign function to a gene by demonstrating that DNA lesions (mutations) in the gene have a quantifiable effect on the organism, including but not limited to: its development; hormone biosynthesis and response; growth and growth habit (plant architecture); mRNA expression profiles; protein expression profiles; ability to resist diseases; tolerance of abiotic stresses; ability to acquire nutrients; photosynthetic efficiency; altered primary and secondary metabolism; and the composition of various plant organs. Biochemistry can assign function by demonstrating that the protein encoded by the gene, typically when expressed in a heterologous organism, possesses a certain enzymatic activity, alone or in combination with other proteins. Molecular genetics can assign function by overexpressing or underexpressing the gene in the native plant or in heterologous organisms, and observing quantifiable effects as described in functional assignment by genetics above. In functional genomics, any or all of these approaches are utilized, often in concert, to assign genes to functions across any of a number of organismal phenotypes.

It is recognized by those skilled in the art that these different methodologies can each provide data as evidence for the function of a particular gene, and that such evidence is stronger with increasing amounts of data used for functional assignment: preferably from a single methodology, more preferably from two methodologies, and even more preferably from more than two methodologies. In addition, those skilled in the art are aware that different methodologies can differ in the strength of the evidence for the assignment of gene function. Typically, but not always, a datum of biochemical, genetic and molecular genetic evidence is considered stronger than a datum of bioinformatic or gene expression evidence. Finally, those skilled in the art recognize that, for different genes, a single datum from a single methodology can differ in terms of the strength of the evidence provided by each distinct datum for the assignment of the function of these different genes.

The objective of crop trait functional genomics is to identify crop trait genes, i.e. genes capable of conferring useful agronomic traits in crop plants. Such agronomic traits include, but are not limited to: enhanced yield, whether in quantity or quality; enhanced nutrient acquisition and enhanced metabolic efficiency; enhanced or altered nutrient composition of plant tissues used for food, feed, fiber or processing; enhanced utility for agricultural or industrial processing; enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. The deployment of such identified trait genes by either transgenic or non-transgenic means could materially improve crop plants for the benefit of agriculture.

II. Identifying, Cloning and Sequencing cDNAs

The cloning and sequencing of the cDNAs of the present invention are described in the Examples below.

The isolated nucleic acids and proteins of the present invention are usable over a range of plants, monocots and dicots, in particular monocots such as rice, wheat, barley and maize. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum* sp., or teosinte. In a most preferred embodiment, the cereal is rice. Other plants genera include, but are not limited to, *Cucurbita, Rosa, Vitis, Juglans, Gragaria, Lotus, Medicago, Onobrychis, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium,* and *Triticum.*

The present invention also provides a method of genotyping a plant or plant part comprising a nucleic acid molecule of the present invention. Optionally, the plant is a monocot such as, but not limited rice or wheat. Genotyping provides a means of distinguishing homologs of a chromosome pari and can be used to differentiate segregants in a plant population. Molecular marker methods can be used in phylogenetic studies, characterizing genetic relationships among crop varieties, identifying crosses or somatic hybrids, localizing chromosomeal segments affecting mongenic traits, map based cloning, and the study of quantitative inheritance (see *Plant Molecular Biology: A Laboratory Manual,* Chapter 7, Clark ed., Springer-Verlag, Berlin 1997; Paterson, A. H., "The DNA Revolution", chapter 2 in *Genome Mapping in Plants,* Paterson, A. H. ed., Academic Press/R. G. Lands Co., Austin, Tex. 1996).

The method of genotyping may employ any number of molecular marker analytical techniques such as, but not limited to, restriction length polymorphisms (RFLPs). As is well known in the art, RFLPs are produced by differences in the DNA restriction fragment lengths resulting from nucleotide differences between alleles of the same gene. Thus, the present invention provides a method of following segregation of a gene or nucleic acid of the present invention or chromosomal sequences genetically linked by using RFLP analysis. Linked chromosomal sequences are within 50 centiMorgans (50 cM), within 40 or 30 cM, preferably within 20 or 10 cM, more preferably within 5, 3, 2, or 1 cM of the nucleic acid of the invention.

III. Traits of Interest

The present invention encompasses the identification and isolation of cDNAs encoding genes of interest in the expression of abiotic stress tolerance. Abiotic stresses such as, but not limited to, cold, heat, drought or salt stress can significantly affect the growth and/or yield of plants. Altering the expression of genes related to these traits can be used to improve or modify the rice plants and/or grain, as desired. Examples describe the isolated genes of interest and methods of analyzing the alteration of expression and their effects on the plant characteristics.

One aspect of the present invention provides compositions and methods for altering (i.e. increasing or decreasing) the level of nucleic acid molecules and polypeptides of the present invention in plants. In particular, the nucleic acid molecules and polypeptides of the invention are expressed constitutively, temporally or spatially, e.g. at developmental stages, in certain tissues, and/or quantities, which are uncharacteristic of non-recombinantly engineered plants. Therefore, the present invention provides utility in such exemplary applications as altering the specified characteristics identified above.

VI. Controlling Gene Expression in Transgenic Plants

The invention further relates to transformed cells comprising the nucleic acid molecules, transformed plants, seeds, and plant parts, and methods of modifying phenotypic traits of interest by altering the expression of the genes of the invention.

A. Modification of Coding Sequences and Adjacent Sequences

The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators that operate within plant cells. This includes promoters and transcription terminators that may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (*Science* 261: 754–756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably, as little adjacent microbial sequence as possible should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF that should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome-binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (*N.A.R.* 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

Position Before the Initiating ATG in 14 Maize Genes:

|   | -10 | -9 | -8 | -7 | -6 | -5 | -4 | -3 | -2 | -1 |
|---|-----|----|----|----|----|----|----|----|----|----|
| C | 3   | 8  | 4  | 6  | 2  | 5  | 6  | 0  | 10 | 7  |
| T | 3   | 0  | 3  | 4  | 3  | 2  | 1  | 1  | 1  | 0  |
| A | 2   | 3  | 1  | 4  | 3  | 2  | 3  | 7  | 2  | 3  |
| G | 6   | 3  | 6  | 0  | 6  | 5  | 4  | 6  | 1  | 5  |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

B. Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and *Arabidopsis*—Callis et al., *J. Biol. Chem.* 265:12486–12493 (1990) and Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Seed-specific Expression

Seed specific expression can be obtained by utilizing expression vectors or cassettes with seed-specific promoters such as but not limited to, the ADPgpp, gamma-zein, glutelin, RS-4, globulin, or oleosin promoter.

e. Inducible Expression, PR-1 Promoters:

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the Arabidopsis PR-1 promoter described in Lebel et al., Plant J. 16:223–233 (1998) may be used. The promoter of choice is preferably excised from its source by restriction enzymes, but can alternatively be PCR-amplified using primers that carry appropriate terminal restriction sites. Should PCR-amplification be undertaken, the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., Plant Cell 4: 645–656 (1992)). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is accomplished by cleavage with XhoI and blunting with T4 polymerase, followed by cleavage with HindIII, and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from Aspergillus nidulans (Caddick et al. (1998) Nat. Biotechnol 16:177–180). In A. nidulans, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) Nat. Biotechnol 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) The Plant Journal 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled either by a promoter known in the art or described here. This expression cassette is also comprised in the plant comprising a nucleic acid sequence of the invention fused to the 6xGAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is the promoter of the maize metallothionein-like (MTL) gene described by de Framond (FEBS 290: 103–106 (1991)) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis,* which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and correct mRNA polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126–6130 (1989)); potyvirus leaders, for example, TEV leader (Tobacco Etch Virus) (Allison et al., 1986); MDMV leader (Maize Dwarf Mosaic Virus); *Virology* 154:9–20); human immunoglobulin heavy-chain binding protein (BiP) leader, (Macejak, D. G., and Sarnow, P., *Nature* 353: 90–94 (1991); untranslated leader from the coat protein mRNA of alfalfa mosaic virus (AMV RNA 4), (Jobling, S. A., and Gehrke, L., *Nature* 325:622–625 (1987); tobacco mosaic virus leader (TMV), (Gallie, D. R. et al., *Molecular Biology of RNA,* pages 237–256 (1989); and Maize Chlorotic Mottle Virus leader (MCMV) (Lommel, S. A. et al., *Virology* 81:382–385 (1991). See also, Della-Cioppa et al., *Plant Physiology* 84:965–968 (1987).

In addition to incorporating one or more of the aforementioned elements into the 5' regulatory region of a target expression cassette of the invention, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1LucR98 via cleavage at the NheI site located at −53 to −58. Roth et al., *Plant Cell* 3: 317 (1991). The derived Bz1 core promoter fragment thus extends from −53 to +227 and includes the Bz1 intron-1 in the 5' untranslated region. Also useful for the invention is a minimal promoter created by use of a synthetic TATA element. The TATA element allows recognition of the promoter by RNA polymerase factors and confers a basal level of gene expression in the absence of activation (see generally, Mukumoto (1993) *Plant Mol Biol* 23: 995–1003; Green (2000) *Trends Biochem Sci* 25: 59–63)

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins that is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

C. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

1. Vectors Suitable for *Agrobacterium* Transformation

Many vectors are available for transformation using *Agrobacterium tumefaciens.* These typically carry at least one T-DNA border sequence and include vectors such as pBIN19

(Bevan, Nucl. Acids Res. (1984)). Below, the construction of two typical vectors suitable for *Agrobacterium* transformation is described.

a. pCIB200 and pCIB2001:

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives Thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for Non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

D. Transformation

Once a nucleic acid sequence of the invention has been cloned into an expression system, it is transformed into a plant cell. The receptor and target expression cassettes of the present invention can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for *Japonica*-types and *Indica*-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using *Agrobacterium* has also been described. See, WO 94/00977 and U.S. Pat. No. 5,591,616, both of which are incorporated herein by reference. See also, Negrotto et al., *Plant Cell Reports* 19: 798–803 (2000), incorporated herein by reference.

For this example, rice (*Oryza sativa*) is used for generating transgenic plants. Various rice cultivars can be used (Hiei et al., 1994, Plant Journal 6:271–282; Dong et al., 1996, Molecular Breeding 2:267–276; Hiei et al., 1997, Plant Molecular Biology, 35:205–218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for ~2 days at 28° C. *Agrobacterium* is re-suspended in liquid MS-CIM medium. The *Agrobacterium* culture is diluted to an OD600 of 0.2–0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., In Vitro Cell. Dev. Biol.-Plant 37:127–132), cultures are transferred to selection medium containing Mannose as a carbohydrate source (MS with 2% Mannose, 300 mg/liter Ticarcillin) after 7 days, and cultured for 3–4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse ($T_0$ generation) grown to maturity, and the $T_1$ seed is harvested.

3. Transformation of Plastids

Seeds of *Nicotiana tabacum* c.v. 'Xanthi nc' are germinated seven per plate in a 1" circular array on T agar medium and bombarded 12–14 days after sowing with 1 μm tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings are incubated on T medium for two days after which leaves are excised and placed abaxial side up in bright light (350–500 μmol photons/m$^2$/s) on plates of RMOP medium (Svab, Z., Hajdukiewicz, P. and Maliga, P. (1990) *PNAS* 87, 8526–8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

V. Breeding and Seed Production

A. Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

B. Seed Production

In seed production, germination quality and uniformity of seeds are essential product characteristics. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

VI. Alteration of Expression of Nucleic Acid Molecules

The alteration in expression of the nucleic acid molecules of the present invention is achieved in one of the following ways:

A. "Sense" Suppression

Alteration of the expression of a nucleotide sequence of the present invention, preferably reduction of its expression, is obtained by "sense" suppression (referenced in e.g. Jorgensen et al. (1996) Plant Mol. Biol. 31, 957–973). In this case, the entirety or a portion of a nucleotide sequence of the present invention is comprised in a DNA molecule. The DNA molecule is preferably operatively linked to a promoter functional in a cell comprising the target gene, preferably a plant cell, and introduced into the cell, in which the nucleotide sequence is expressible. The nucleotide sequence is inserted in the DNA molecule in the "sense orientation", meaning that the coding strand of the nucleotide sequence can be transcribed. In a preferred embodiment, the nucleotide sequence is fully translatable and all the genetic information comprised in the nucleotide sequence, or portion thereof, is translated into a polypeptide. In another preferred embodiment, the nucleotide sequence is partially translatable and a short peptide is translated. In a preferred embodiment, this is achieved by inserting at least one premature stop codon in the nucleotide sequence, which bring translation to a halt. In another more preferred embodiment, the nucleotide sequence is transcribed but no translation product is being made. This is usually achieved by removing the start codon, e.g. the "ATG", of the polypeptide encoded by the nucleotide sequence. In a further preferred embodiment, the DNA molecule comprising the nucleotide sequence, or a portion thereof, is stably integrated in the genome of the plant cell. In another preferred embodiment, the DNA molecule comprising the nucleotide sequence, or a portion thereof, is comprised in an extrachromosomally replicating molecule.

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 70% identical to the nucleotide sequence the expression of which is reduced, more preferably it is at least 80% identical, yet more preferably at least 90% identical, yet more preferably at least 95% identical, yet more preferably at least 99% identical.

B. "Anti-sense" Suppression

In another preferred embodiment, the alteration of the expression of a nucleotide sequence of the present invention, preferably the reduction of its expression is obtained by "anti-sense" suppression. The entirety or a portion of a nucleotide sequence of the present invention is comprised in a DNA molecule. The DNA molecule is preferably operatively linked to a promoter functional in a plant cell, and introduced in a plant cell, in which the nucleotide sequence is expressible. The nucleotide sequence is inserted in the DNA molecule in the "anti-sense orientation", meaning that the reverse complement (also called sometimes non-coding strand) of the nucleotide sequence can be transcribed. In a preferred embodiment, the DNA molecule comprising the nucleotide sequence, or a portion thereof, is stably integrated in the genome of the plant cell. In another preferred embodiment the DNA molecule comprising the nucleotide sequence, or a portion thereof, is comprised in an extrachromosomally replicating molecule. Several publications describing this approach are cited for further illustration (Green, P. J. et al., Ann. Rev. Biochem. 55:569–597 (1986); van der Krol, A. R. et al, Antisense Nuc. Acids & Proteins, pp. 125–141 (1991); Abel, P. P. et al., PNASroc. Natl. Acad. Sci. USA 86:6949–6952 (1989); Ecker, J. R. et al., Proc. Natl. Acad. Sci. USANAS 83:5372–5376 (August 1986)).

In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 70% identical to the nucleotide sequence the expression of which is reduced, more preferably it is at least 80% identical, yet more preferably at least 90% identical, yet more preferably at least 95% identical, yet more preferably at least 99% identical.

C. Homologous Recombination

In another preferred embodiment, at least one genomic copy corresponding to a nucleotide sequence of the present invention is modified in the genome of the plant by homologous recombination as further illustrated in Paszkowski et al., EMBO Journal 7:4021–26 (1988). This technique uses the property of homologous sequences to recognize each other and to exchange nucleotide sequences between each by a process known in the art as homologous recombination. Homologous recombination can occur between the chromosomal copy of a nucleotide sequence in a cell and an incoming copy of the nucleotide sequence introduced in the cell by transformation. Specific modifications are thus accurately introduced in the chromosomal copy of the nucleotide sequence. In one embodiment, the regulatory elements of the nucleotide sequence of the present invention are modified. Such regulatory elements are easily obtainable by screening a genomic library using the nucleotide sequence of the present invention, or a portion thereof, as a probe. The existing regulatory elements are replaced by different regulatory elements, thus altering expression of the nucleotide sequence, or they are mutated or deleted, thus abolishing the expression of the nucleotide sequence. In another embodiment, the nucleotide sequence is modified by deletion of a part of the nucleotide sequence or the entire nucleotide sequence, or by mutation. Expression of a mutated polypeptide in a plant cell is also contemplated in the present invention. More recent refinements of this technique to disrupt endogenous plant genes have been described (Kempin et al., Nature 389:802–803 (1997) and Miao and Lam, Plant J., 7:359–365 (1995).

In another preferred embodiment, a mutation in the chromosomal copy of a nucleotide sequence is introduced by transforming a cell with a chimeric oligonucleotide composed of a contiguous stretch of RNA and DNA residues in a duplex conformation with double hairpin caps on the ends. An additional feature of the oligonucleotide is for example the presence of 2'-O-methylation at the RNA residues. The RNA/DNA sequence is designed to align with the sequence of a chromosomal copy of a nucleotide sequence of the present invention and to contain the desired nucleotide change. For example, this technique is further illustrated in U.S. Pat. No. 5,501,967 and Zhu et al. (1999) Proc. Natl. Acad. Sci. USA 96: 8768–8773.

D. Ribozymes

In a further embodiment, the RNA coding for a polypeptide of the present invention is cleaved by a catalytic RNA, or ribozyme, specific for such RNA. The ribozyme is expressed in transgenic plants and results in reduced amounts of RNA coding for the polypeptide of the present invention in plant cells, thus leading to reduced amounts of polypeptide accumulated in the cells. This method is further illustrated in U.S. Pat. No. 4,987,071.

E. Dominant-Negative Mutants

In another preferred embodiment, the activity of the polypeptide encoded by the nucleotide sequences of this invention is changed. This is achieved by expression of dominant negative mutants of the proteins in transgenic plants, leading to the loss of activity of the endogenous protein.

F. Aptamers

In a further embodiment, the activity of polypeptide of the present invention is inhibited by expressing in transgenic plants nucleic acid ligands, so-called aptamers, which specifically bind to the protein. Aptamers are preferentially obtained by the SELEX (Systematic Evolution of Ligands by EXponential Enrichment) method. In the SELEX method, a candidate mixture of single stranded nucleic acids having regions of randomized sequence is contacted with the protein and those nucleic acids having an increased affinity to the target are partitioned from the remainder of the candidate mixture. The partitioned nucleic acids are amplified to yield a ligand enriched mixture. After several iterations a nucleic acid with optimal affinity to the polypeptide is obtained and is used for expression in transgenic plants. This method is further illustrated in U.S. Pat. No. 5,270,163.

G. Zinc Finger Proteins

A zinc finger protein that binds a nucleotide sequence of the present invention or to its regulatory region is also used to alter expression of the nucleotide sequence. Preferably, transcription of the nucleotide sequence is reduced or increased. Zinc finger proteins are for example described in Beerli et al. (1998) *PNAS* PNAS 95:14628–14633., or in WO 95/19431, WO 98/54311, or WO 96/06166, all incorporated herein by reference in their entirety.

H. dsRNA

Alteration of the expression of a nucleotide sequence of the present invention is also obtained by dsRNA interference as described for example in WO 99/32619, WO 99/53050 or WO 99/61631, all incorporated herein by reference in their entirety. In another preferred embodiment, the alteration of the expression of a nucleotide sequence of the present invention, preferably the reduction of its expression, is obtained by double-stranded RNA (dsRNA) interference. The entirety or, preferably a portion of a nucleotide sequence of the present invention is comprised in a DNA molecule. The size of the DNA molecule is preferably from 100 to 1000 nucleotides or more; the optimal size to be determined empirically. Two copies of the identical DNA molecule are linked, separated by a spacer DNA molecule, such that the first and second copies are in opposite orientations. In the preferred embodiment, the first copy of the DNA molecule is in the reverse complement (also known as the non-coding strand) and the second copy is the coding strand; in the most preferred embodiment, the first copy is the coding strand, and the second copy is the reverse complement. The size of the spacer DNA molecule is preferably 200 to 10,000 nucleotides, more preferably 400 to 5000 nucleotides and most preferably 600 to 1500 nucleotides in length. The spacer is preferably a random piece of DNA, more preferably a random piece of DNA without homology to the target organism for dsRNA interference, and most preferably a functional intron which is effectively spliced by the target organism. The two copies of the DNA molecule separated by the spacer are operatively linked to a promoter functional in a plant cell, and introduced in a plant cell, in which the nucleotide sequence is expressible. In a preferred embodiment, the DNA molecule comprising the nucleotide sequence, or a portion thereof, is stably integrated in the genome of the plant cell. In another preferred embodiment the DNA molecule comprising the nucleotide sequence, or a portion thereof, is comprised in an extrachromosomally replicating molecule. Several publications describing this approach are cited for further illustration (Waterhouse et al. (1998) PNAS 95:13959–13964; Chuang and Meyerowitz (2000) PNAS 97:4985–4990; Smith et al. (2000) Nature 407:319–320). Alteration of the expression of a nucleotide sequence by dsRNA interference is also described in, for example WO 99/32619, WO 99/53050 or WO 99/61631, all incorporated herein by reference in their entirety In transgenic plants containing one of the DNA molecules described immediately above, the expression of the nucleotide sequence corresponding to the nucleotide sequence comprised in the DNA molecule is preferably reduced. Preferably, the nucleotide sequence in the DNA molecule is at least 70% identical to the nucleotide sequence the expression of which is reduced, more preferably it is at least 80% identical, yet more preferably at least 90% identical, yet more preferably at least 95% identical, yet more preferably at least 99% identical.

I. Insertion of a DNA Molecule (Insertional Mutagenesis)

In another preferred embodiment, a DNA molecule is inserted into a chromosomal copy of a nucleotide sequence of the present invention, or into a regulatory region thereof. Preferably, such DNA molecule comprises a transposable element capable of transposition in a plant cell, such as e.g. Ac/Ds, Em/Spm, mutator. Alternatively, the DNA molecule comprises a T-DNA border of an *Agrobacterium* T-DNA. The DNA molecule may also comprise a recombinase or integrase recognition site which can be used to remove part of the DNA molecule from the chromosome of the plant cell. Methods of insertional mutagenesis using T-DNA, transposons, oligonucleotides or other methods known to those skilled in the art are also encompassed. Methods of using T-DNA and transposon for insertional mutagenesis are described in Winkler et al. (1989) Methods Mol. Biol. 82:129–136 and Martienssen (1998) PNAS 95:2021–2026, incorporated herein by reference in their entireties.

J. Deletion Mutagenesis

In yet another embodiment, a mutation of a nucleic acid molecule of the present invention is created in the genomic copy of the sequence in the cell or plant by deletion of a portion of the nucleotide sequence or regulator sequence. Methods of deletion mutagenesis are known to those skilled in the art. See, for example, Miao et al, (1995) Plant J. 7:359.

In yet another embodiment, this deletion is created at random in a large population of plants by chemical mutagenesis or irradiation and a plant with a deletion in a gene of the present invention is isolated by forward or reverse genetics. Irradiation with fast neutrons or gamma rays is known to cause deletion mutations in plants (Silverstone et al, (1998) Plant Cell, 10:155–169; Bruggemann et al., (1996) Plant J., 10:755–760; Redei and Koncz in *Methods in Arabidopsis Research,* World Scientific Press (1992), pp. 16–82). Deletion mutations in a gene of the present invention can be recovered in a reverse genetics strategy using PCR with pooled sets of genomic DNAs as has been shown in *C. elegans* (Liu et al., (1999), Genome Research, 9:859–867.). A forward genetics strategy would involve mutagenesis of a line displaying PTGS followed by screening the M2 progeny for the absence of PTGS. Among these mutants would be expected to be some that disrupt a gene of the present invention. This could be assessed by Southern blot or PCR for a gene of the present invention with genomic DNA from these mutants.

K. Overexpression in a Plant Cell

In yet another preferred embodiment, a nucleotide sequence of the present invention encoding a polypeptide is overexpressed. Examples of nucleic acid molecules and expression cassettes for over-expression of a nucleic acid molecule of the present invention are described above. Methods known to those skilled in the art of over-expression of nucleic acid molecules are also encompassed by the present invention.

In a preferred embodiment, the expression of the nucleotide sequence of the present invention is altered in every cell of a plant. This is for example obtained though homologous recombination or by insertion in the chromosome. This is also for example obtained by expressing a sense or antisense RNA, zinc finger protein or ribozyme under the control of a promoter capable of expressing the sense or antisense RNA, zinc finger protein or ribozyme in every cell of a plant. Constitutive expression, inducible, tissue-specific or developmentally regulated expression are also within the scope of the present invention and result in a constitutive, inducible, tissue-specific or developmentally-regulated alteration of the expression of a nucleotide sequence of the present invention in the plant cell. Constructs for expression of the sense or antisense RNA, zinc finger protein or ribozyme, or for over-expression of a nucleotide sequence of the present invention, are prepared and transformed into a plant cell according to the teachings of the present invention, e.g. as described infra.

VII. Polypeptides

The present invention further relates to isolated polypeptides comprising the amino acid sequence of SEQ ID NO:2. In particular, isolated polypeptides comprising the amino acid sequence of SEQ ID NO:2, and variants having conservative amino acid modifications. One skilled in the art will recognize that individual substitutions, deletions or additions to a nucleic acid, peptide, polypeptide or protein sequence which alters, adds or deletes a single amino acid or a small percent of amino acids in the encoded sequence is a "conservative modification" where the modification results in the substitution of an amino acid with a chemically similar amino acid. Conservative modified variants provide similar biological activity as the unmodified polypeptide. Conservative substitution tables listing functionally similar amino acids are known in the art. See Crighton (1984) *Proteins,* W. H. Freeman and Company.

In a preferred embodiment, a polypeptide having substantial similarity to a polypeptide sequence listed in SEQ ID NO:2, or exon, domain, or feature thereof, is an allelic variant of the polypeptide sequence listed in red SEQ ID NO:2. In another preferred embodiment, a polypeptide having substantial similarity to a polypeptide sequence listed in SEQ ID NO:2, or exon, domain, or feature thereof, is a naturally occurring variant of the polypeptide sequence listed in SEQ ID NO:2. In another preferred embodiment, a polypeptide having substantial similarity to a polypeptide sequence listed in SEQ ID NO:2, or exon, domain, or feature thereof, is a polymorphic variant of the polypeptide sequence listed in SEQ ID NO:2.

In an alternate preferred embodiment, the sequence having substantial similarity contains a deletion or insertion of at least one amino acid. In a more preferred embodiment, the deletion or insertion is of less than about ten amino acids. In a most preferred embodiment, the deletion or insertion is of less than about three amino acids.

In a preferred embodiment, the sequence having substantial similarity encodes a substitution in at least one amino acid.

Embodiments of the present invention also contemplate an isolated polypeptide containing a polypeptide sequence including:
- (f) a polypeptide sequence listed in SEQ ID NO:2, or exon, domain, or feature thereof;
- (g) a polypeptide sequence having substantial similarity to (a);
- (h) a polypeptide sequence encoded by a nucleotide sequence identical to or having substantial similarity to a nucleotide sequence listed in SEQ ID NO:1, or an exon, domain, or feature thereof, or a sequence complementary thereto;
- (i) a polypeptide sequence encoded by a nucleotide sequence capable of hybridizing under medium stringency conditions to a nucleotide sequence listed in SEQ ID NO:1, or to a sequence complementary thereto; and
- (j) a functional fragment of (a), (b), (c) or (d).

In another preferred embodiment, the polypeptide having substantial similarity is an allelic variant of a polypeptide sequence listed in SEQ ID NO:2, or a fragment, domain, repeat, feature, or chimeras thereof. In another preferred embodiment, the isolated nucleic acid includes a plurality of regions from the polypeptide sequence encoded by a nucleotide sequence identical to or having substantial similarity to a nucleotide sequence listed in SEQ ID NO:1, or fragment, domain, or feature thereof, or a sequence complementary thereto.

In another preferred embodiment, the polypeptide is a polypeptide sequence listed in SEQ ID NO:2. In another preferred embodiment, the polypeptide is a functional fragment or domain. In yet another preferred embodiment, the polypeptide is a chimera, where the chimera may include functional protein domains, including domains, repeats, post-translational modification sites, or other features. In a more preferred embodiment, the polypeptide is a plant polypeptide. In a more preferred embodiment, the plant is a dicot. In a more preferred embodiment, the plant is a gymnosperm. In a more preferred embodiment, the plant is a monocot. In a more preferred embodiment, the monocot is a cereal. In a more preferred embodiment, the cereal may be, for example, maize, wheat, barley, oats, rye, millet, sorghum, triticale, secale, einkorn, spelt, emmer, teff, milo, flax, gramma grass, *Tripsacum,* and teosinte. In a most preferred embodiment, the cereal is rice.

In a preferred embodiment, the polypeptide is expressed in a specific location or tissue of a plant. In a more preferred embodiment, the location or tissue is for example, but not limited to, epidermis, vascular tissue, meristem, cambium, cortex or pith. In a most preferred embodiment, the location or tissue is leaf or sheath, root, flower, and developing ovule or seed. In a more preferred embodiment, the location or tissue may be, for example, epidermis, root, vascular tissue, meristem, cambium, cortex, pith, leaf, and flower. In a more preferred embodiment, the location or tissue is a seed.

In a preferred embodiment, the polypeptide sequence encoded by a nucleotide sequence having substantial similarity to a nucleotide sequence listed in SEQ ID NO:1 or a fragment, domain, or feature thereof or a sequence complementary thereto, includes a deletion or insertion of at least one nucleotide. In a more preferred embodiment, the deletion or insertion is of less than about thirty nucleotides. In a most preferred embodiment, the deletion or insertion is of less than about five nucleotides.

In a preferred embodiment, the polypeptide sequence encoded by a nucleotide sequence having substantial similarity to a nucleotide sequence listed in SEQ ID NO:1, or fragment, domain, or feature thereof or a sequence complementary thereto, includes a substitution of at least one codon. In a more preferred embodiment, the substitution is conservative.

In a preferred embodiment, the polypeptide sequences having substantial similarity to the polypeptide sequence listed in SEQ ID NO:2, or a fragment, domain, repeat, feature, or chimeras thereof includes a deletion or insertion of at least one amino acid.

The polypeptides of the invention, fragments thereof or variants thereof can comprise any number of contiguous amino acid residues from a polypeptide of the invention, wherein the number of residues is selected from the group of integers consisting of from 10 to the number of residues in a full-length polypeptide of the invention. Preferably, the portion or fragment of the polypeptide is a functional protein. The present invention includes active polypeptides having specific activity of at least 20%, 30%, or 40%, and preferably at least 505, 60%, or 70%, and most preferably at least 805, 90% or 95% that of the native (non-synthetic) endogenous polypeptide. Further, the substrate specificity ($k_{cat}/K_m$) is optionally substantially similar to the native (non-synthetic), endogenous polypeptide. Typically the $K_m$ will be at least 30%, 40%, or 50% of the native, endogenous polypeptide; and more preferably at least 605, 70%, 80%, or 90%. Methods of assaying and quantifying measures of activity and substrate specificity are well known to those of skill in the art.

The isolated polypeptides of the present invention will elicit production of an antibody specifically reactive to a polypeptide of the present invention when presented as an immunogen. Therefore, the polypeptides of the present invention can be employed as immunogens for constructing antibodies immunoreactive to a protein of the present invention for such purposes, but not limited to, immunoassays or protein purification techniques. Immunoassays for determining binding are well known to those of skill in the art such as, but not limited to, ELISAs or competitive immunoassays.

Embodiments of the present invention also relate to chimeric polypeptides encoded by the isolated nucleic acid molecules of the present disclosure including a chimeric polypeptide containing a polypeptide sequence encoded by an isolated nucleic acid containing a nucleotide sequence including:
- (g) a nucleotide sequence listed in SEQ ID NO:1, or exon, domain, or feature thereof;
- (h) a nucleotide sequence having substantial similarity to (a);
- (i) a nucleotide sequence capable of hybridizing to (a);
- (j) a nucleotide sequence complementary to (a), (b) or (c); and
- (k) a nucleotide sequence which is the reverse complement of (a), (b) or (c);
- (l) or a functional fragment thereof.

A polypeptide containing a polypeptide sequence encoded by an isolated nucleic acid containing a nucleotide sequence, its complement, or its reverse complement, encoding a polypeptide including a polypeptide sequence including:

(g) a polypeptide sequence listed in SEQ ID NO:2, or a domain, repeat, feature, or chimeras thereof;

(h) a polypeptide sequence having substantial similarity to (a);

(i) a polypeptide sequence encoded by a nucleotide sequence identical to or having substantial similarity to a nucleotide sequence listed in SEQ ID NO:1, or an exon, domain, or feature thereof, or a sequence complementary thereto;

(j) a polypeptide sequence encoded by a nucleotide sequence capable of hybridizing under medium stringency conditions to a nucleotide sequence listed in SEQ ID NO:1, or to a sequence complementary thereto; and (k) a functional fragment of (a), (b), (c) or (d);

(l) or a functional fragment thereof.

The isolated nucleic acid molecules of the present invention are useful for expressing a polypeptide of the present invention in a recombinantly engineered cell such as a bacteria, yeast, insect, mammalian or plant cell. The cells produce the polypeptide in a non-natural condition (e.g. in quantity, composition, location and/or time) because they have been genetically altered to do so. Those skilled in the art are knowledgeable in the numerous expression systems available for expression of nucleic acids encoding a protein of the present invention, and will not be described in detail below.

Briefly, the expression of isolated nucleic acids encoding a polypeptide of the invention will typically be achieved, for example, by operably linking the nucleic acid or cDNA to a promoter (constitutive or regulatable) followed by incorporation into an expression vector. The vectors are suitable for replication and/or integration in either prokaryotes or eukaryotes. Commonly used expression vectors comprise transcription and translation terminators, initiation sequences and promoters for regulation of the expression of the nucleic acid molecule encoding the polypeptide. To obtain high levels of expression of the cloned nucleic acid molecule, it is desirable to use expression vectors comprising a strong promoter to direct transcription, a ribosome-binding site for translation initiation, and a transcription/translation terminator. One skilled in the art will recognize that modifications may be made to the polypeptide of the present invention without diminishing its biological activity. Some modifications may be made to facilitate the cloning, expression or incorporation of the polypeptide of the invention into a fusion protein. Such modification are well known in the art and include, but are not limited to, a methionine added at the amino terminus to provide an initiation site, or additiona amino acids (e.g. poly Histadine) placed on either terminus to create conveniently located purification sequences. Restriction sites or termination codons can also be introduced into the vector.

In a preferred embodiment, the expression vector includes one or more elements such as, for example, but not limited to, a promoter-enhancer sequence, a selection marker sequence, an origin of replication, an epitope-tag encoding sequence, or an affinity purification-tag encoding sequence. In a more preferred embodiment, the promoter-enhancer sequence may be, for example, the CaMV 35S promoter, the CaMV 19S promoter, the tobacco PR-1a promoter, the ubiquitin promoter, and the phaseolin promoter. In another embodiment, the promoter is operable in plants, and more preferably, a constitutive or inducible promoter. In another preferred embodiment, the selection marker sequence encodes an antibiotic resistance gene. In another preferred embodiment, the epitope-tag sequence encodes V5, the peptide Phe-His-His-Thr-Thr, hemagglutinin, or glutathione-S-transferase. In another preferred embodiment the affinity purification-tag sequence encodes a polyamino acid sequence or a polypeptide. In a more preferred embodiment, the polyamino acid sequence is polyhistidine. In a more preferred embodiment, the polypeptide is chitin binding domain or glutathione-S-transferase. In a more preferred embodiment, the affinity purification-tag sequence comprises an intein encoding sequence.

Prokaryotic cells may be used a host cells, for example, but not limited to, *Escherichia coli,* and other microbial strains known to those in the art. Methods for expressing proteins in prokaryotic cells are well known to those in the art and can be found in many laboratory manuals such as *Molecular Cloning: A Laboratory Manual,* by J. Sambrook et al. (1989, Cold Spring Harbor Laboratory Press). A variety of promoters, ribosome binding sites, and operators to control expression are available to those skilled in the art, as are selectable markers such as antibiotic resistance genes. The type of vector chosen is to allow for optimal growth and expression in the selected cell type.

A variety of eukaryotic expression systems are available such as, but not limited to, yeast, insect cell lines, plant cells and mammalian cells. Expression and synthesis of heterologous proteins in yeast is well known (see Sherman et al., *Methods in Yeast Genetics,* Cold Spring Harbor Laboratory Press, 1982). Commonly used yeast strains widely used for production of eukaryotic proteins are *Saccharomyces cerevisiae* and *Pichia pastoris,* and vectors, strains and protocols for expression are available from commercial suppliers (e.g., Invitrogen).

Mammalian cell systems may be transfected with expression vectors for production of proteins. Many suitable host cell lines are available to those in the art, such as, but not limited to the HEK293, BHK21 and CHO cells lines. Expression vectors for these cells can include expression control sequences such as an origin of replication, a promoter, (e.g., the CMV promoter, a HSV tk promoter or phosphoglycerate kinase (pgk) promoter), an enhancer, and protein processing sites such as ribosome binding sites, RNA splice sites, polyadenylation sites, and transcription terminator sequences. Other animal cell lines useful for the production of proteins are available commercially or from depositories such as the American Type Culture Collection.

Expression vectors for expressing proteins in insect cells are usually derived from the SF9 baculovirus or other viruses known in the art. A number of suitable insect cell lines are available including but not limited to, mosquito larvae, silkworm, armyworm, moth and *Drosophila* cell lines.

Methods of transfecting animal and lower eukaryotic cells are known. Numerous methods are used to make eukaryotic cells competent to introduce DNA such as but not limited to: calcium phosphate precipitation, fusion of the recipient cell with bacterial protoplasts containing the DNA, treatment of the recipient cells with liposomes containing the DNA, DEAE dextrin, electroporation, biolistics, and microinjection of the DNA directly into the cells. Tranfected cells are cultured using means well known in the art (see, Kuchler, R. J., *Biochemical Methods in Cell Culture and Virology,* Dowden, Hutchinson and Ross, Inc. 1997).

Once a polypeptide of the present invention is expressed it may be isolated and purified from the cells using methods known to those skilled in the art. The purification process may be monitored using Western blot techniques or radioimmunoassay or other standard immunoassay techniques. Protein purification techniques are commonly known and used by those in the art (see R. Scopes, *Protein Purification: Principles and Practice,* Springer-Verlag, New York 1982: Deutscher, *Guide to Protein Purification,* Academic Press (1990). Embodiments of the present invention provide a method of producing a recombinant protein in which the expression vector includes one or more elements including a promoter-enhancer sequence, a selection marker sequence, an origin of replication, an epitope-tag encoding sequence, and an affinity purification-tag encoding sequence. In one preferred embodiment, the nucleic acid construct includes an epitope-tag encoding sequence and the isolating step includes use of an antibody specific for the epitope-tag. In another preferred embodiment, the nucleic acid construct contains a polyamino acid encoding sequence and the isolating step includes use of a resin comprising a polyamino acid binding substance, preferably where the polyamino acid is polyhistidine and the polyamino binding resin is nickel-charged agarose resin. In yet another preferred embodiment, the nucleic acid construct contains a polypeptide encoding sequence and the isolating step includes the use of a resin containing a polypeptide binding substance, preferably where the polypeptide is a chitin binding domain and the resin contains chitin-sepharose.

The polypeptides of the present invention cam be synthesized using non-cellular synthetic methods known to those in the art. Techniques for solid phase synthesis are described by Barany and Mayfield, Solid-Phase Peptide Synthesis, pp. 3–284 in the *Peptides: Analysis, Synthesis, Biology, Vol. 2, Special Methods in Peptide Synthesis, Part A;* Merrifield, et al., *J. Am. Chem. Soc.* 85:2149–56 (1963) and Stewart et al., *Solid Phase Peptide Synthesis,* $2^{nd}$ ed. Pierce Chem. Co., Rockford, Ill. (1984).

The present invention further provides a method for modifying (i.e. increasing or decreasing) the concentration or composition of the polypeptides of the invention in a plant or part thereof. Modification can be effected by increasing or decreasing the concentration and/or the composition (i.e. the ration of the polypeptides of the present invention) in a plant. The method comprised introducing into a plant cell with an expression cassette comprising a nucleic acid molecule of the present invention, or an nucleic acid encoding a RAR1 sequence as described above to obtain a transformed plant cell or tissue, culturing the transformed plant cell or tissue. The nucleic acid molecule can be under the regulation of a constitutive or inducible promoter. The method can further comprise inducing or repressing expression of a nucleic acid molecule of a sequence in the plant for a time sufficient to modify the concentration and/or composition in the plant or plant part.

A plant or plant part having modified expression of a nucleic acid molecule of the invention can be analyzed and selected using methods known to those skilled in the an such as, but not limited to, Southern blot, DNA sequencing, or PCR analysis using primers specific to the nucleic acid molecule and detecting amplicons produced therefrom.

In general, concentration or composition in increased or decreased by at least 5%, 10%, 20%, 30%, 40%, 50%, 60%, 70%, 80% or 90% relative to a native control plant, plant part or cell lacking the expression cassette.

VIII. BOS1 Promoter

In addition, the present invention also provides promoters capable of conferring abiotic stress responsive expression to an associated nucleotide sequence of interest. Preferred are promoter sequences obtainable from the *Arabidopsis thaliana* BOS1 gene. Nucleotide sequences comprising functional and/or structural equivalents thereof are also embraced by the invention. The present invention thus relates to nucleotide sequences that function as promoters of transcription of associated nucleotide sequences. The promoter region may also include elements that act as regulators of gene expression such as activators, enhancers, and/or repressors and may include the 5' non-translated leader sequence of the transcribed mRNA and/or introns and, optionally, exons.

Abiotic stress responsive inducible expression means that the nucleotide sequence of interest is preferentially expressed when an abiotic stress according to the invention is applied. Thus, the nucleotide sequence according to the invention is useful for abiotic stress responsive inducible expression of an associated nucleotide sequence of interest, which preferably is a coding sequence. It is known to the skilled artisan that the associated coding sequence of interest can be expressed in sense or in antisense orientation. Further, the coding sequence of interest may be of heterologous or homologous origin with respect to the plant to be transformed. In case of a homologous coding sequence, the nucleotide sequence according to the invention is useful for ectopic expression of said sequence. In one particular embodiment of the invention expression of the coding sequence of interest under control of a nucleotide sequence according to the invention suppresses its own expression and that of the original copy of the gene by a process called co-suppression.

The promoters of the present invention can be obtained, for example, from *Arabidopsis thaliana* genomic DNA by probing an *Arabidopsis* genomic library with a cDNA according to the invention using methods known in the art. It is obvious to a person skilled in the art that genomic DNA from any other organism, particularly from plants, can be used to obtain a lipoxygenase promoter from any organism of interest. This genomic DNA is then sequenced and aligned to the cDNA sequence. Basically, all nucleotide sequences upstream of the start codon are considered to be part of the lipoxygenase promoter region. In addition, introns and, optionally, exons can be added to this region to form a functional promoter that confers abiotic stress responsvie inducible expression to an associated coding region.

In a preferred embodiment of the invention, the BOS1 promoter is a component of SEQ ID NO:4. Other preferred embodiments of the invention are the nucleotide sequences depicted in SEQ ID NOs:4 or 3.

Based on the sequence information given in SEQ ID NO:4 or 3, the DNA sequences of the invention can be obtained, for example, by PCR using a nucleic acid molecule of SEQ ID NO:4 or genomic DNA from a plant or any other organism of interest as template. The person skilled in the art knows how to arrive at such sequences using methods known in the art. These sequences then can be fused to reporter genes to demonstrate promoter activity. For example, chimeric genes can be constructed that include part of the 5' regulatory sequence of the BOS1 gene fused to the GFP coding sequence. To this end, SEQ ID NO:3 can be used as template for the polymerase chain reaction (PCR). Gene-specific primers can be designed to amplify the 5' promoter region of the gene. Using combinations of, for example, the BOS1 promoter reverse primer (SEQ ID NO:14) with BOS1 promoter forward primer (SEQ ID NO:13) the regulatory sequences that are ~1.2 kb and ~2 kb upstream of the initiating methionine are isolated. The nucleotide sequence of the PCR fragment amplified with BOS1 promoter forward primer and BOS1 promoter reverse primer is shown in SEQ ID NO:4. For ease of cloning the primers consist, for example, of gene specific sequences and attB recombination sites for the GATEWAY™ cloning technology (Life Technologies, GIBCO BRL, Rockville, Md. USA).

Transgenic plants are then produced using, for example, Agrobacterium-mediated transformation techniques. Expression of the gene fusion protein can be monitored in transformants by confocal imaging using a Leica-TCS confocal laser scanning microscope and a PLAPO ×100 oil immersion objective (Leica Microsystems, Heidelberg, Germany) with the following filter settings: excitation 476/488 nm; GFP-emission 515–552 nm, chlorophyll-emission 673–695 nm. GFP fluorescence and chlorophyll autofluorescence are recorded simultaneously using independent 2-channel-detection. Confocal imaging of leaves from transgenic rice plants expressing the pRCI promoter::GFP construct can be carried out to assay promoter activity in response to abiotic and biotic inducers.

It is apparent to the skilled artisan that, based on the nucleotide sequences shown in SEQ ID NO:4 or 3, any primer combination of interest can be chosen to PCR amplify DNA fragments of various lengths that can be used according to the invention. Thus, any region of interest can be amplified from SEQ ID NOs:4 or 3. For example, primers can be designed to specifically amplify intron 1 or intron 2 or the 5' upstream region. The 5' upstream region is defined herein as the region between the putative TATA box and the putative start codon of the lipoxygenase protein.

Further, it might also be desirable to combine any of these sequences with the 3' untranslated region of the lipoxygenase cDNA sequence (of SEQ ID NO:5).

The invention thus includes fragments derived from the rice RCI-1 lipoxygenase gene that function according to the invention, i.e. are capable of conferring chemically induced but not wound- or pathogen induced expression of an associated nucleotide sequence. This can be tested by generating such promoter fragments, fusing them to a selectable or screenable marker gene and assaying the fusion constructs for retention of promoter activity in transient expression assays with protoplasts or in stably transformed plants. Such assays are within the skill of the ordinary artisan. Preferred nucleic acid molecule fragments of the invention are of at least about 500 bases, particularly of between about 1000 bases and about 1500 bases, more particularly of about 2000 bases and most particularly of between about 3000 bases and about 4500 bases in length.

It is also clear to the skilled artisan that mutations, insertions, deletions end/or substitutions of one or more nucleotides can be introduced into the nucleotide sequences of SEQ ID NOs:3 or 4 or longer or shorter fragments derived from the sequence information thereof using methods known in the art. In addition, an unmodified or modified nucleotide sequence of the present invention can be varied by shuffling the sequence of the invention. To test for a function of variant nucleotide sequences according to the invention, the sequence of interest is operably linked to a selectable or screenable marker gene and expression of the marker gene is tested in transient expression assays with protoplasts or in stably transformed plants. It is known to the skilled artisan that nucleotide sequences capable of driving expression of an associated nucleotide sequence are build in a modular way. Accordingly, expression levels from shorter nucleic acid molecule fragments may be different than the one from the longest fragment and may be different from each other. For example, deletion of a down-regulating upstream element will lead to an increase in the expression levels of the associated nucleotide sequence while deletion of an up-regulating element will decrease the expression levels of the associated nucleotide sequence.

Another way of identifying promoter elements necessary for regulated expression of an associated nucleotide sequence is the so-called linker-scanning analysis. Linker-scanning mutagenesis allows for the identification of short defined motifs whose mutation alters the promoter activity. Accordingly, a set of linker-scanning mutant promoters fused to the coding sequence of the GUS reporter gene or another marker gene can be constructed using methods known in the art. These construct are then transformed into Arabidopsis, for example, and GUS activity is assayed in several independent transgenic lines. The effect of each mutation on promoter activity is then compared to an equivalent number of transgenic lines containing an unmutated rice lipoxygenase gene promoter. It is expected, that when a motif is mutated that is involved in chemically, but not wound or pathogen-inducible expression, that the level of expression of the reporter gene is modified. If, for example, a higher average induction of GUS activity by a chemical inducer is detected than the one from the control construct most likely a negative regulatory element had been mutated in this construct. If, on the other hand, a complete loss of inducibility of GUS activity by a chemical regulator according to the invention is observed, most likely a positive regulatory element necessary chemical induction has been mutated. In a next step, particularly in the case of the putative positive regulatory element, the wild-type sequences corresponding to the mutated fragments are fused to a minimal promoter and the newly created promoter is tested for the ability to confer regulated expression to an associated marker gene.

Embraced by the present invention are also functional equivalents of the RCI-1 promoters of the present invention, i.e. nucleotide sequences that hybridize under stringent conditions to any one of SEQ ID NO:3 or 4. A stringent hybridization is performed at a temperature of 65° C., preferably 60° C. and most preferably 55° C. in double strength (2×) citrate buffered saline (SSC) containing 0.1% SDS followed by rinsing of the support at the same temperature but with a buffer having a reduced SSC concentration. Such reduced concentration buffers are typically one-tenth strength SSC (0.1×SSC) containing 0.1% SDS, preferably 0.2×SSC containing 0.1% SSC and most preferably half strength SSC (0.5×SSC) containing 0.1% SDS. In fact, functional equivalents to all or part of the RCI-1 lipoxygenase promoter from other organisms can be found by hybridizing any one of SEQ ID NO:1, SEQ ID NO:2, or SEQ ID NO:3 or the 4.5 PstI/PstI fragment of plasmid pBSK+LOX4A which has been deposited under accession no DSM 13524 with genomic DNA isolated from an organism of interest, particularly from another monocot. The skilled artisan knows how to proceed to find such sequences as there are many ways known in the art to identify homologous sequences from other organisms. Such newly identified DNA molecules then can be sequenced and the sequence can be compared to any one of SEQ ID NO:3 or 4, and tested for promoter activity. Within the scope of the present invention are DNA molecules having at least 75%, preferably 80%, more preferably 90%, and most preferably 95% sequence identity to the nucleotide sequence of any one of SEQ ID NOs:3 or 4 over a length of at least 50 nucleotides. The percentage of sequence identity is determined using computer programs that are based on dynamic programming algorithms. Computer programs that are preferred within the scope of the present invention include the BLAST (Basic Local Alignment Search Tool) search programs designed to explore all of the available sequence databases regardless of whether the query is protein or DNA. Version BLAST 2.0 (Gapped BLAST) of this search tool has been made publicly available on the Internet. It uses a heuristic algorithm that seeks local as opposed to global alignments and is therefore able to detect relationships among sequences which share only isolated regions. The scores assigned in a BLAST search have a well-defined statistical interpretation. Said programs are preferably run with optional parameters set to the default values.

If desired, the promoters of the present invention can be fused with the nucleotide sequence encoding a transit peptide according to the invention for example, by using the nucleotide sequence depicted in SEQ ID NO:4, for abiotic stress responsive expression of an associated coding region of interest in plastids, particularly in chloroplasts.

It is another object of the present invention to provide recombinant nucleic acid molecules comprising a promoter according to the invention operably linked to a nucleotide sequence of interest. The nucleotide sequence of interest can, for example, code for a ribosomal RNA, an antisense RNA or any other type of RNA that is not translated into protein. In another preferred embodiment of the invention the nucleotide sequence of interest is translated into a protein product. The nucleotide sequence associated with the promoter sequence may be of homologous or heterologous origin with respect to the plant to be transformed. The sequence may also be entirely or partially synthetic. Regardless of the origin, the associated nucleotide sequence will be expressed in the transformed plant in accordance with the expression properties of the promoter to which it is linked. In case of homologous nucleotide sequences associated with the promoter sequence, the promoter according to the invention is useful for ectopic expression of said homologous sequences. Ectopic expression means that the nucleotide sequence associated with the promoter sequence is expressed in tissues and organs and/or at times where said sequence may not be expressed under control of its own promoter. In one particular embodiment of the invention, expression of nucleotide sequence associated with the promoter sequence suppresses its own expression and that of the original copy of the gene by a process called cosuppression.

In a preferred embodiment of the invention the associated nucleotide sequence may code for a protein that is desired to be expressed in aa abiotic stress responsive inducible fashion. Such nucleotide sequences preferably encode proteins conferring a desirable phenotypic trait to the plant transformed therewith. Examples are nucleotide sequences encoding proteins conferring abiotic stress tolerance, antibiotic resistance, virus resistance, insect resistance, disease resistance, or resistance to other pests, herbicide tolerance, improved nutritional value, improved performance in an industrial process or altered reproductive capability. The associated nucleotide sequence may also be one that is transferred to plants for the production of commercially valuable enzymes or metabolites in the plant. Embraced by the present invention are also selectable or screenable marker genes, i.e. genes comprising a nucleotide sequence of the invention operably linked to a coding region encoding a selectable or screenable trait.

Examples of selectable or screenable marker genes are described below. For certain target species, different antibiotic or herbicide selection markers may be preferred. Selection markers used routinely in transformation include the nptII gene that confers resistance to kanamycin, paromomycin, geneticin and related antibiotics (Vieira and Messing, 1982, Gene 19: 259–268; Bevan et al., 1983, Nature 304: 184–187) the bacterial aadA gene (Goldschmidt-Clermont, 1991, Nucl. Acids Res. 19: 4083–4089), encoding aminoglycoside 3'-adenylyltransferase and conferring resistance to streptomycin or spectinomycin, the hph gene which confers resistance to the antibiotic hygromycin (Blochlinger and Diggelmann, 1984, Mol. Cell. Biol. 4: 2929–2931), and the dhfr gene, which confers resistance to methotrexate (Bourouis and Jarry, 1983, EMBO J. 2: 1099–1104). Other markers to be used include a phosphinothricin acetyltransferase gene, which confers resistance to the herbicide phosphinothricin (White et al., 1990, Nucl. Acids Res. 18: 1062; Spencer et al. 1990, Theor. Appl. Genet. 79: 625–631), a mutant EPSP synthase gene encoding glyphosate resistance (Hinchee et al., 1988, Bio/Technology 6: 915–922), a mutant acetolactate synthase (ALS) gene which confers imidazolione or sulfonylurea resistance (Lee et al., 1988, EMBO J. 7: 1241–1248), a mutant psbA gene conferring resistance to atrazine (Smeda et al., 1993, Plant Physiol. 103: 911–917), or a mutant protoporphyrinogen oxidase gene as described in EP 0 769 059. Selection markers resulting in positive selection, such as a phosphomannose isomerase gene, as described in patent application WO 93/05163, are also used.

Identification of transformed cells may also be accomplished through expression of screenable marker genes such as genes coding for chloramphenicol acetyl transferase (CAT), β-glucuronidase (GUS), luciferase (LUC), and green fluorescent protein (GFP) or any other protein that confers a phenotypically distinct trait to the transformed cell.

It is a further objective of the invention to provide recombinant expression vectors comprising a nucleotide sequence of the invention fused to an associated nucleotide sequence of interest. In these vectors, foreign nucleic acid molecules can be inserted into a polylinker region such that these exogenous sequences can be expressed in a suited host cell which may be, for example, of bacterial or plant origin. For example, the plasmid pBI101 derived from the *Agrobacterium tumefaciens* binary vector pBIN19 allows cloning and testing of promoters using beta-glucuronidase (GUS) expression signal (Jefferson et al, 1987, EMBO J 6: 3901–3907). The size of the vector is 12.2 kb. It has a low-copy RK2 origin of replication and confers kanamycine resistance in both bacteria and plants. There are numerous other expression vectors known to the person skilled in the art that can be used according to the invention.

The present invention also provides transgenic plants comprising the recombinant DNA sequences of the invention. The invention thus relates to plant cells, to plants derived from such cells, to plant material, to the progeny and to seeds derived from such plants, and to agricultural products with improved properties obtained by any one of the transformation methods described below. Plants transformed in accordance with the present invention may be monocots or dicots and include, but are not limited to, rice, maize, wheat, barley, rye, sweet potato, sweet corn, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar-beet, sunflower, rapeseed, clover, tobacco, carrot, cotton, alfalfa, potato, eggplant, cucumber, *Arabidopsis thaliana*, and woody plants such as coniferous and deciduous trees. Preferred plants to be transformed are rice, maize, wheat, barley, cabbage, cauliflower, pepper, squash, melon, soybean, tomato, sugar-beet, sunflower or cotton, but especially rice, maize, wheat, *Sorghum bicolor*, orchardgrass, sugar beet and soybean. The recombinant DNA sequences of the invention can be introduced into the plant cell by a number of well-known methods. Those skilled in the art will appreciate that the choice of such method might depend on the type of plant which is targeted for transformation, i.e., monocot or dicot. Suitable methods of transforming plant cells include microinjection (Crossway et al., 1986, Bio Techniques 4:320–334), electroporation (Riggs and Bates, 1986, Proc. Natl. Acad. Sci., USA 83:5602–5606), *Agrobacterium*-mediated transformation (Hinchee et al., 1988, Bio/Technology 6:915–922; EP 0 853 675), direct gene transfer (Paszkowski et al., 1984, EMBO J. 3:2717–2722), and ballistic particle acceleration using devices available from Agracetus, Inc., Madison, Wis. and Dupont, Inc., Wilmington, Del. (see, for example, U.S. Pat. No. 4,945,050 and McCabe et al., 1988, Bio/Technology 6:923–926). The cells to be transformed may be differentiated leaf cells, embryogenic cells, or any other type of cell.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by J. Sambrook, et al., Molecular Cloning: *A Laboratory Manual*, 3d Ed., Cold Spring Harbor, N.Y.: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1

Expression Vectors and Tranformation of Plants

Binary destination vectors for plant transformation consist of a binary backbone and a T-DNA portion. The binary backbone contains the sequences necessary for selection and growth in *Escherichia coli* DH-5α (Invitrogen) and *Agrobacterium tumefaciens* LBA4404, including the bacterial spectinomycin antibiotic resistance aadA gene from *E. coli* transposon Tn7, origins of replication for *E. coli* (ColE1) and *A. tumefaciens* (VS1), and the *A. tumefaciens* virG gene. The T-DNA portion was flanked by the right and left border sequences and includes the Positech™ (Syngenta) plant selectable marker and a gene expression cassette which varies depending on the application. The Positech™ plant selectable marker in this instance consists of a rice ACT1 (actin) promoter driving expression of the PMI (phosphomannose isomerase) gene, followed by the cauliflower mosaic virus transcriptional terminator, and confers resistance to mannose.

The gene expression cassette portion of the binary destination vectors varies depending on the application. In general, the cassette consists of a promoter designed to express the gene in certain tissues of the plant, followed by cloning sites (in some cases interrupted by a segment of spacer DNA), and finally by the *A. tumefaciens* nos 3' end transcriptional terminator. The promoters used are designed to express the gene of interest in specific target tissues (eg. endosperm: rice RS-4, wheat glutelin, maize ADPgpp or γ-zein, or barley α-thionin; eg. embryo: maize globulin or oleosin; eg. aleurone: barley α-amylase; eg. root: maize MSR1 and MRS3; eg. green tissue: maize PEPC) or constitutively (eg. maize UBI plus intron), depending on the gene of interest. The cloning site contains either unique restriction enzyme sites (for conventional cloning) and/or a Gateway™ recombination-based cloning cassette (Invitrogen), in either the forward or reverse orientation. In gene expression cassettes designed for double-stranded interfering RNA (dsRNA) production, the cloning site is divided by a spacer region (eg. first intron of the rice SH1 gene). The spacer permits the cloning of two gene fragments one in the forward and one in the reverse orientation. Antisense (reverse orientation expression) is another technology available for silencing genes of interest.

Transformation of the nucleic acid molecules of the present invention into plants is performed using methods described above in the Detailed Description.

Example 2

Abiotic Stress Tolerance cDNAs and Analysis

Table 1 lists candidate rice genes for biotic or abiotic stress tolerance described in this application.

TABLE 1

Abiotic Stress Tolerance Genes

| Gene | SEQ ID Nos: | Putative Function & Similar Genes | Homology Reference and % Homology |
|---|---|---|---|
| BOS1 | 1–2 | drought tolerance; bacterial infection tolerance | dehydration induced myb-related proteins from the resurrection plant *Craterostigma plantagineum*, Cpm7 (NCBI #T09737), Cpm5 (NCBI#T09736) and Cpm10 (NCBI#T09735). These Cpm proteins show 76–80% identity to the BOS1 protein over a stretch of the first 152 amino acids in the amino terminus of the BOS1 protein |

The abiotic stress tolerance genes are evaluated for their effect(s) in transformed plants by testing the transgenic transformed plants or progeny plants as compared with non-transgenic plants. The plants are tested for their altered tolerance cold, drought, salt and heat using methods known to those skilled in the art, and examples of such assays are described below.

Tolerance to salt is measured by using any salt tolerance assay known to those skilled in the art. In particular, the salt tolerance assay is performed essentially as follows:

Seeds from transformed plants and untransformed parental lines are sown on filter paper soaked with Yoshida solution placed in petri dishes. After 7 days of growth in the climate chamber seedlings (about 4 cm shoot length and 4 cm root length) will be exposed to salt stress as follows: seedlings will be transferred to 24 well plates supplemented with Yoshida solution (control) or Yoshida solution enriched with two different salt concentrations (as below). To ensure the contact of the entire root with the solution a piece of moistened absorbent cotton is placed on top of the root within the well flooded with the solution. Alternatively, the seeds may be grown in sand as a growth medium.

Control: Yoshida solution without supplementary salt

1) Yoshida solution enriched with NaCl 3.2 mg/l (48 mM)+ CaCl$_2$ 3.6 mg/l (24 mM). This salt concentration evoked 50% growth reduction in shoot length.

2) Yoshida solution enriched with NaCl 6.4 mg/l (96 mM)+ CaCl$_2$ 7.1 mg/l (48 mM).

Tissue is harvested at: 0, 6, 12, 24, and 36 hours. After exposure, the seedlings are separated into shoots and roots, or whole seedlings (whichever you prefer) and then immediately frozen in liquid nitrogen for RNA extraction and analysis. Total RNA extraction is performed using any known method in the art such as, an RNA extraction kit from Qiagen.

Alternatively, seedlings are observed for enhanced or decreased tolerance to grown under salt stress as compared to the untransformed parental variety online. Samples are also taken for analysis of protein expression.

Figure 2:
FIG. 2 shows the bos1 mutant (7675–30) to have increased susceptiblity to another necrotrophic pathogen, *Alternaria brassicicola* compared to wild type (7675–29).
Figure 2:
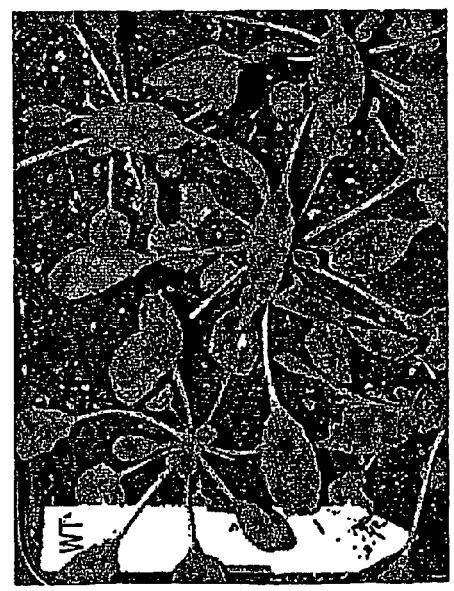
Figure 2:
Figure 2:
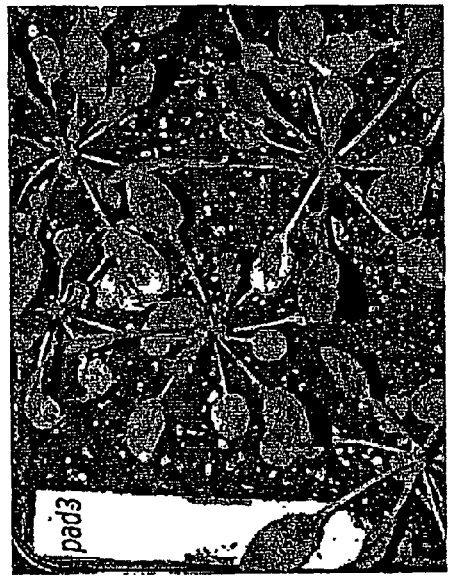
Figure 3:
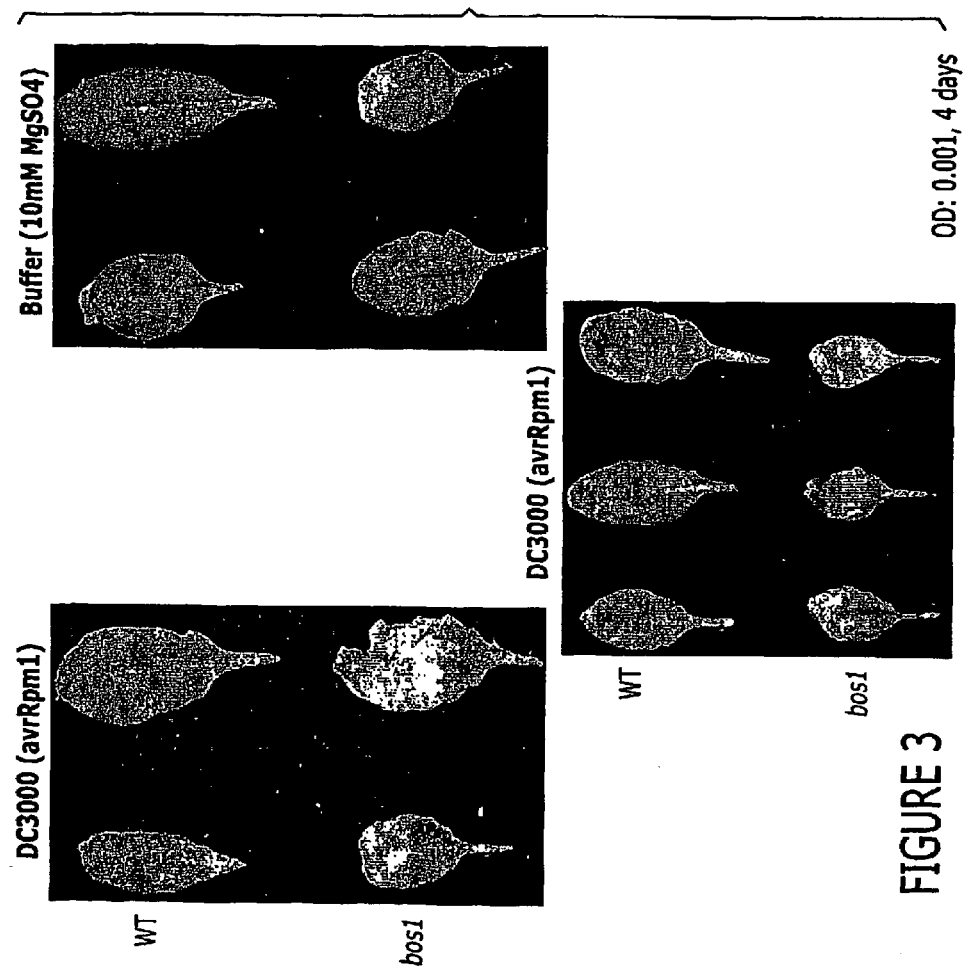
FIG. 3 shows the bos1 mutant to have increased susceptibility to a bacterial pathogen, *Pseudomonas syringae* compared to wild type.
Figure 4:
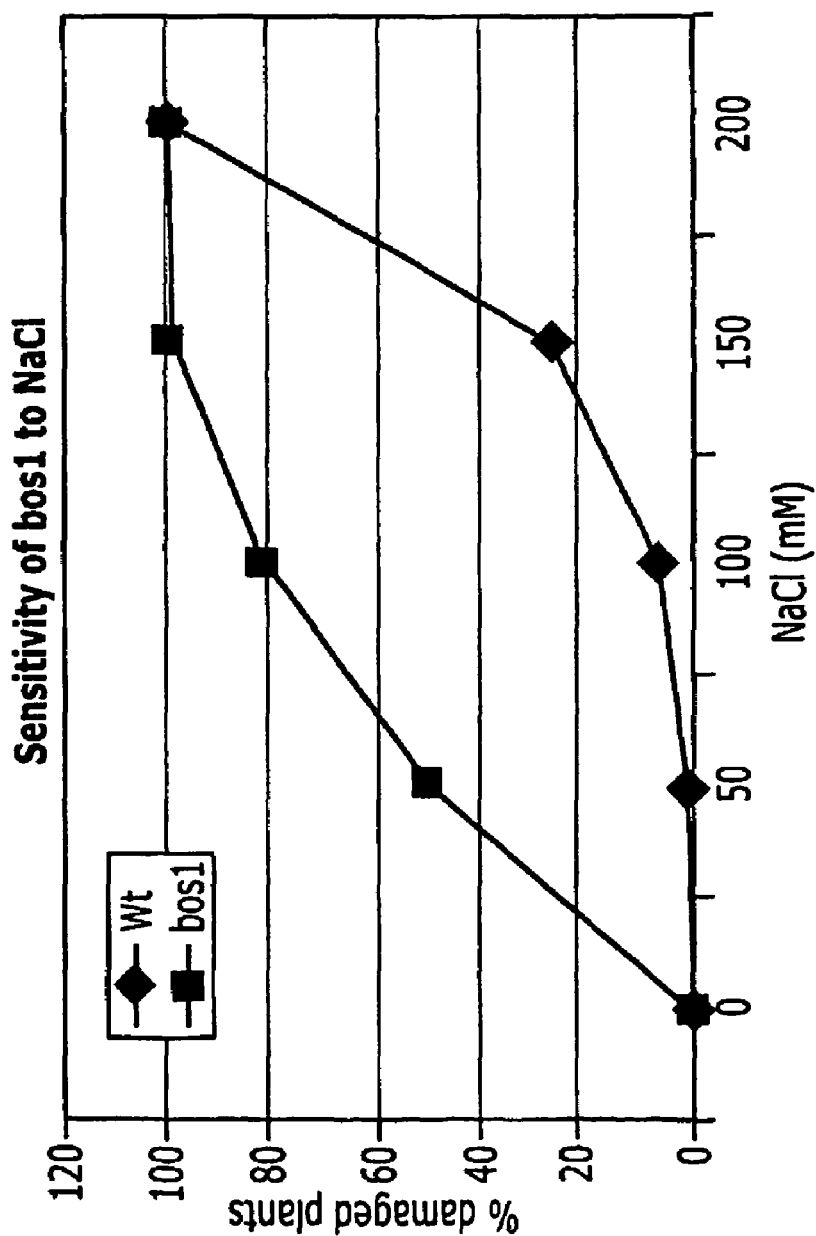
FIG. 4 is a graph showing that the survival of bos1 plants was significantly reduced following exposure to salt stress. When grown in the presence of 100 mM NaCl, only 18.75% of bos1 plants survived compared to 93.75% of wild type plants.
Figure 5:
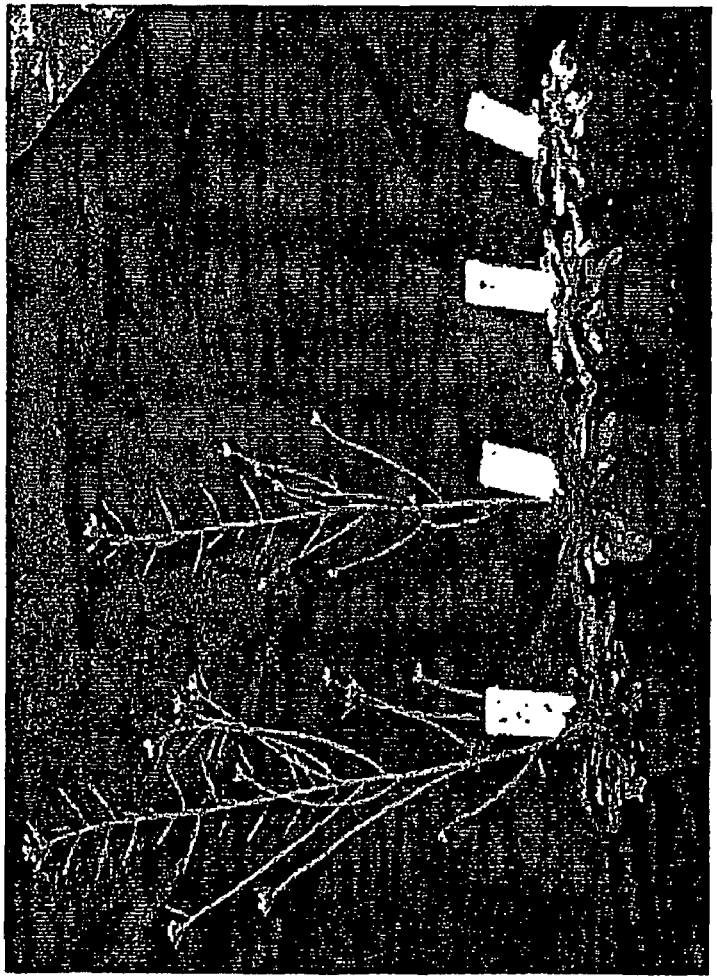
FIG. 5 shows that the bos1 plants are sensitive to drought stress compared to wild type plants.
Figure 6:
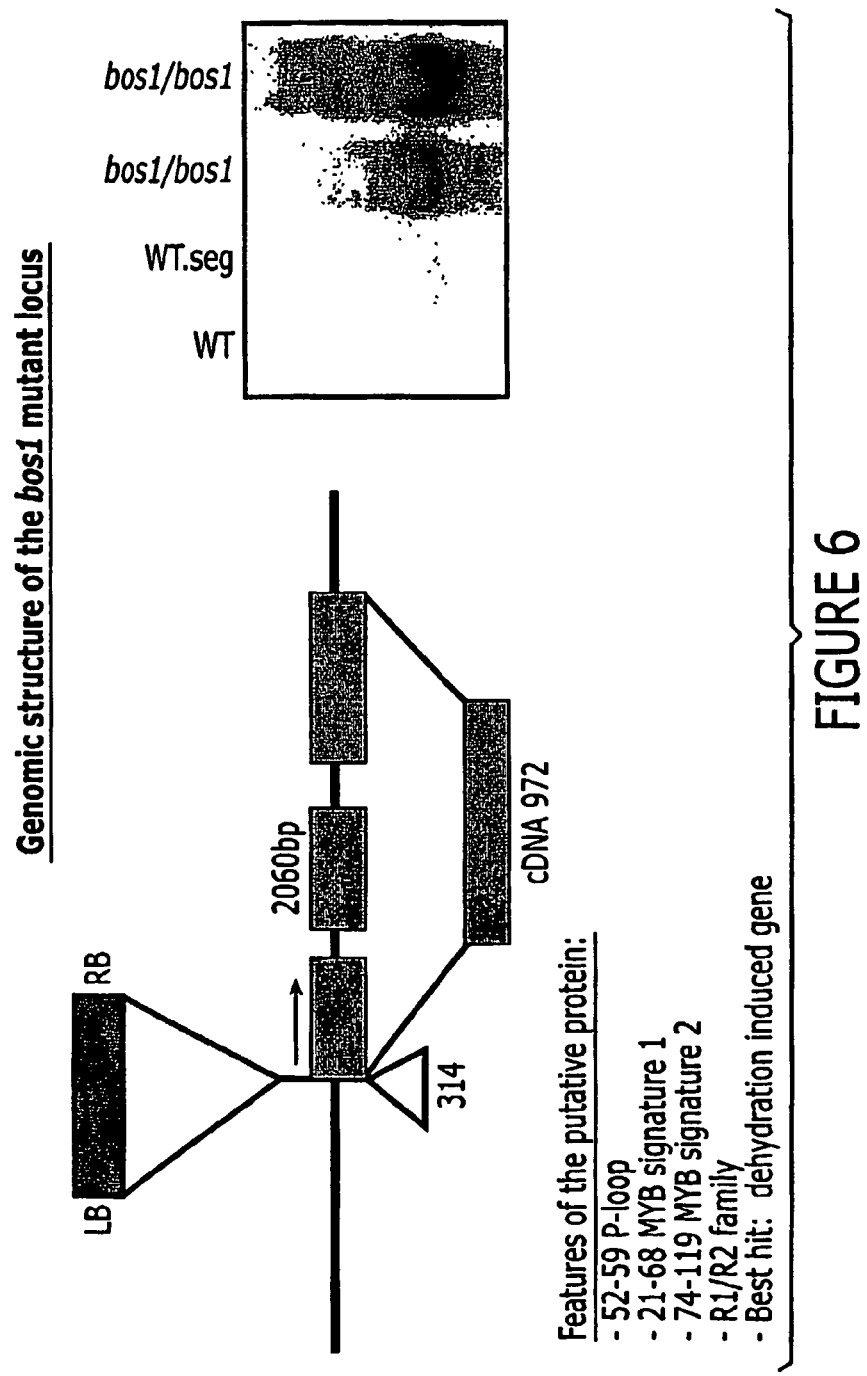
FIG. 6 shows that the bos1 mutant was affected in the normal expression of the gene encoding for a MYB transcription factor (referred to as AtMYB108 in the public data base, referred to herein as BOS1) due to a T-DNA insertion.
Figure 7A:
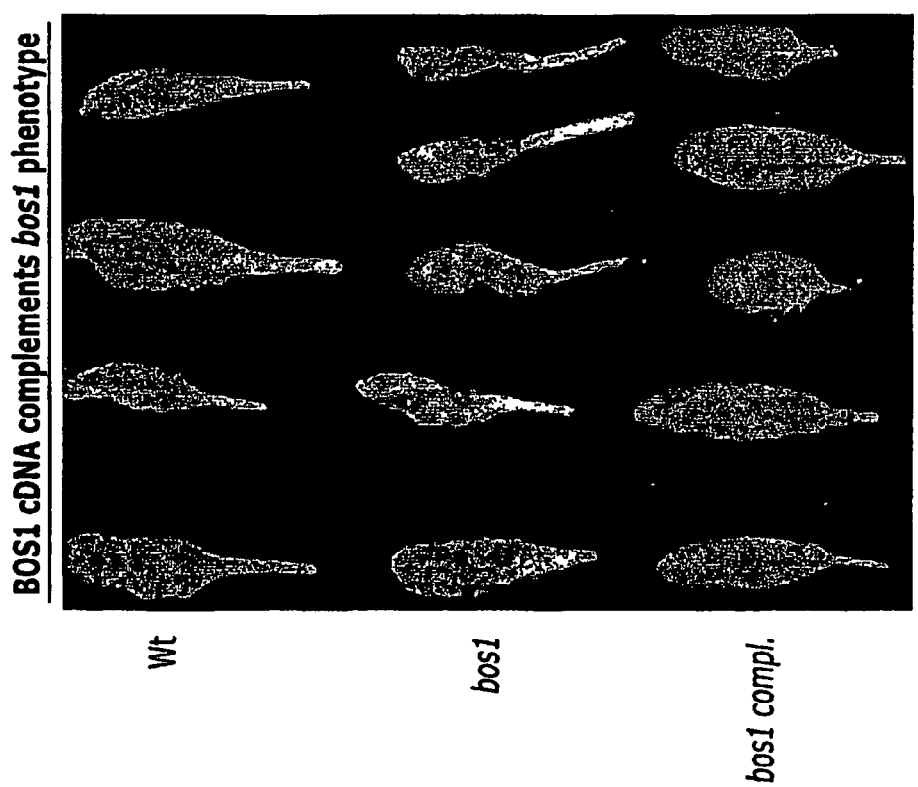
FIGS. 7A & B show that constitutive expression of BOS1 (AtMYB108) under the regulation of the *Arabidopsis* UBQ3 promoter restores the *Botrytis* susceptibility phenotype of the mutant to the wild type level of resistance.
Figure 7B:

Yoshida Solutions ceptible (bos1) mutant from a T-DNA mutagenized population based on its increased susceptibility to *Botrytis cinerea* compared to wild type parental ecotype Col-0 plants (FIG. 1). The mutant was later tested and found to have increased susceptibility to another necrotrophic pathogen, *Alternaria brassicicola* (FIG. 2) and to a bacterial pathogen, *Pseudomonas syringae* (FIG. 3). Interestingly, the survival of bos1 plants was significantly reduced following exposure to drought or salt stress. When grown in the presence of 100 mM NaCl, only 18.75% of bos1 plants survived compared to 93.75% of wild type plants (FIG. 4). Similarly, when water was withheld from soil grown plants up to visible wilting, followed by watering, only 28% of the bos1 plants recovered, compared to 88% recovery in wild type plants (FIG. 5). The mutant (bos1) was affected in the normal expression of the gene encoding for a MYB transcription factor (referred to as AtMYB108 in the public data base, we refer to it as BOS1) due to a T-DNA insertion (FIG. 6). In a preliminary assay, constitutive expression of BOS1 (At-MYB108) under the regulation of the *Arabidopsis* UBQ3 promoter restores the *Botrytis* susceptibility phenotype of the mutant to the wild type level of resistance (FIG. 7). This confirmed that the mutation of the BOS1 (AtMYB108) gene is responsible for the bos1 mutant phenotype. These plants

| Elem. | Chemical names | Stock preparation (g/10 L stock) | Culture solution (ml stock/ 10 L solutions) | Final conc. (mM (ppm)) |
|---|---|---|---|---|
| (Macro) | | | | |
| N | NH$_4$NO$_3$ | 914 | 12.5 | 1.43 mM (114 pm) |
| P | NaH$_2$PO$_4$.2H$_2$O | 403 | 12.5 | 0.33 mM (51 ppm) |
| K | K$_2$SO$_4$ | 714 | 12.5 | 0.51 mM (89 ppm) |
| Ca | CaCl$_2$ | 886 | 12.5 | 1.0 mM (111 ppm) |
| Mg | MgSO$_4$.7H$_2$O | 3240 | 12.5 | 1.6 mM (394 ppm) |
| (Micro)* | | | | |
| Mn | MnCl$_2$.4H$_2$O | 15–20 | | >0.01 mM |
| Mo | (NH$_4$)$_6$.MO$_7$O$_{24}$.4H$_2$O | 1.5 | | $1.5 \times 10^{-4}$ mM |
| B | H$_3$BO$_3$ | 12 | | 0.02 mM |
| Zn | ZnSO$_4$.7H$_2$O | 0.7 | | $3 \times 10^{-4}$ mM |
| Cu | CuSO$_4$.5H$_2$O | 0.31 | | $1.6 \times 10^{-4}$ mM |
| | Citric acid | 119 | 12.5 of mixture | 0.071 mM |
| (Iron)Fe | Iron chelate | | 160 | 12.5 |

*Mix microelements in 10 L distilled water in the order above.
pH, 5.8 adjust with H$_2$SO$_4$ if necessary For drought tolerance, substitute 20% polyethylene glycol (PEG; MW 8000) for the salt solution.

Example 3

BOS1 Identification and Isolation

*Botrytis cinerea* causes the gray mold diseases in horticultural crops resulting in significant pre- and post-harvest loses. It is a necrotrophic fungal pathogen that infects a wide range of plant species in the field, greenhouse and storage. Very little is known about the molecular basis of the host response to *B. cinerea* and other necrotrophic fungal pathogens. Although genetic variation for resistance has been reported, no resistance gene has been identified. In search of a genetic resistance mechanism, we initiated a screen to identify genes mediating resistance to *Botrytis cinerea* and other necrotrophic pathogens. We identified a *botrytis* suswill be assayed for the complementation of the other diseases and abiotic stress response phenotypes of the bos1 mutant.

Plants resistant to one stress are often more resistant to others. In some cases the resistance phenotypes could even transcend the biotic and abiotic stress boundary. This phenomenon, referred to as cross-tolerance could be important for agriculture as crops could be developed to tolerate more than one stress. Phenotypic data from the mutant suggests that the wild type BOS1 gene is involved in regulating responses to both biotic and abiotic stresses and a possibly in cross-regulation between responses to microbial infection and responses to some abiotic stress factors. Importantly, this makes the BOS1 gene a feasible candidate for generating crop varieties with increased tolerance to necrotrophic pathogens such as *Botrytis cinerea, Alternaria* spp, nd also for developing crop varieties with increased tolerance to drought and salt stress.

Example 4

Cloning of the Gene Responsible for the bos1 Phenotype

The bos1 mutant was identified among transgenic *Arabidopsis* lines generated by transforming with *Agrobacterium*. We screened the T-DNA insertion lines for *botrytis* susceptible (bos) mutants. The mutant was found in the family 7675 in a collection generated by Syngenta Biotechnology Inc. as susceptible to *Botrytis cinerea* compared to the wild type parental ecotype Colo-o plants. The *Botrytis* susceptibility assay was done on 3-week old plants either by spraying a spore suspension containing 100,000 spores per ml or drop inoculation of the spore suspension on leaves. Genetic and molecular analysis showed that the T-DNA insert co-segregates with the mutant phenotype. The mutant was affected in the normal expression of the MYB transcription factor due to a T-DNA insertion in the promoter region that leads to an altered expression (FIG. 6). In a preliminary assay constitutive expression of this gene under the regulation of the *Arabidopsis* UBQ3 promoter complements or rescues the bos1 phenotype of the mutant (FIG. 7)

Figure 8:
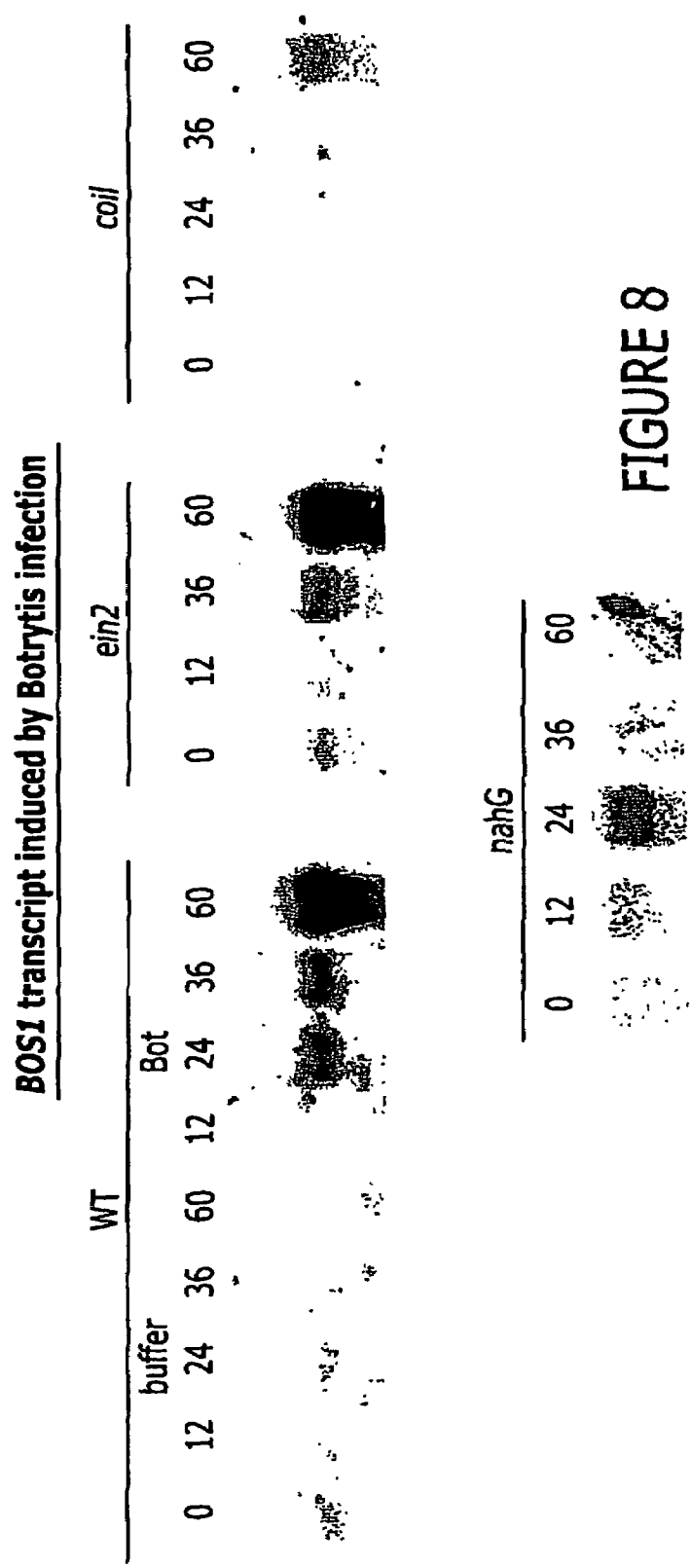
FIG. 8 shows that the BOS1 gene was induced following *Botrytis* infection.

Expression analysis following *Botrytis* infection showed that BOS1 gene was induced following *Botrytis* infection (FIG. 8). However, disease inducibility of BOS1 was delayed and reduced in the coi1 mutant of *Arabidopsis* that is defective in JA perception (Xie et al., Science 280: 1091–4, 1998).

Genomic DNA from the mutant was isolated according to the procedure described (Dellaporta et al., 1983) and used for TAIL PCR (Liu et al., Plant J. 8(3):457–63, 1995) to amplify genomic fragment flanking the left border of the T-DNA. TAIL PCR products contained sequence from the mutagenizing T-DNA and adjacent *Arabidopsis* sequence. The T-DNA inserted in the promoter region of the BOS1 gene (SEQ ID NO:4).

BOS1 cDNA and Genomic Clones

The genomic sequence from TAIL PCR of bos1 mutant was used as the basis for cloning the wild type BOS1 cDNA and genomic clones. The ends of the cDNA were determined by 5'and 3'RACE. Primers were designed based on the genomic sequence obtained from the TAIL PCR product sequence. RACE was performed according to the SMART protocol from Clonetech. Poly A RNA from Col-0 wild type plants was reverse transcribed using oligo dT primers provided by the SMART RACE cDNA Amplification Kit (Clontech). This was used as a template to amplify BOS1 cDNA using sense and antisense gene specific primers:

```
3'RACE Primer1:
5'-GACGTCCGCCGTGGAAACATTACACTT-3'    (SEQ ID NO:5)

3'RACE Primer2:
5'-GGAAGAACGGACAACGAGATCAAGAAC-3'    (SEQ ID NO:6)

5'RACE Primer1:
5'-TAGTACTCCGTTAAGTCTGACGCCGGAGA-3'   (SEQ ID NO:7)

5'RACE Primer2:
5'-ATGCAAGATGACGTGCCGGCTGAT-3'       (SEQ ID NO:8)
```

Once the 5'and 3'ends of the BOS1 cDNA were determined by RACE, gene specific primers were designed to the start and stop codons and used to amplify a full-length cDNA using the following primers:

```
                                     (SEQ ID NO:9)
BOS1cDNA Forward primer:
5'-ATG GAT GAA AAA GGA AGA AGC TTG AAG-3'

(SEQ ID NO:10)
BOS1cDNA Reverse primer:
5'-TCA GAA GCT ACC ATT ATT GTT GAA CTG-3
```

The BOS1 genomic region was cloned by using gene specific primers designed to include 1.5 Kb region upstream of the Start codon and a reverse primer designed to the stop codon.

```
                                     (SEQ ID NO:11)
BOS1 Genomic Forward primer:
5'-TGC ACC AAA CCAA GTAA CAA GAGG-3'

(SEQ ID NO:12)
BOS1 Genomic Reverse primer:
5'-CTA GCTAGCTCAGAAGCTACCATTATTGTT-3'
```

Example 5

Biotic Stress Assay

Fungal culture: *Botrytis* was grown on 2×V8 agar (36% V8 juice, 0.2% CaCO3, 2% Bacto-agar) at 20° C. Fungal cultures were initiated by transferring pieces of agar containing mycelium to fresh 2×V8 agar and incubated at 20–25° C. Conidia were collected from 10 day old cultures by placing agar slices containing fungal material in 1% Sabouraud Maltose Broth (SMB) buffer (DIFCO, Sparks, Md., USA, Becton Dickinson) and vortexing to release the spores. The suspension was passed through miracloth to separate the fungal material from pieces of agar.

Botrytis assay: To infect plants, the fungal spore density was adjusted to $10^5$ spores/ml in SMB buffer and sprayed on four-five week old plants using a Preval sprayer. Single leaf inoculations were done by placing 2–3 μL droplets of spore suspension of *Botrytis* on individual leaves of four-five week old plants. Following inoculation plants were kept under a transparent cover to maintain high humidity and transferred to a growth chamber with 21° C. day and 18° C. night temperature and 12-h light/12-h dark cycle. The light intensity was approximately 200 μE/m²/s. Results of these assays were described above and in the Figures.

Example 6

BOS1 Promoter

The BOS1 promoter was cloned by amplifying the 1.5 KB genomic sequence upstream of the translation start site of the BOS1 coding region (SEQ ID NO:1). This promoter fragment was fused to the GUS reporter gene for the analysis of the regulation of the gene and pattern of expression. The following primers were used to clone the BOS1 promoter.

```
BOS1 Promoter Forward Primer:
5'-TCAATAGAAATCAGAAAACG-3'           (SEQ ID NO:13)

BOS1 Promoter Reverse Primer:
5'-TGA TAT ACA CAG AAG AGA CCA-3'    (SEQ ID NO:14)
```

Example 7

Sequence Analysis

The Alignment of the BOS1 cDNA with the genomic sequence shows that the BOS1 gene is interrupted by 2 introns. The 1.2 Kb long cDNA of BOS1 (SEQ ID NO:1) contains an ORF capable of encoding a protein of 323 amino acids (SEQ ID NO:2) with a predicted molecular mass of 37019.8 Da and a theoretical pI of 4.93. Insertion of the T-DNA in the bos1 mutant occurred in the 5'UTR region. The BOS1 ORF encodes a putative MYB-related protein with an ATP/GTP binding domain at the amino terminus (position 52–59 aa), followed by the two Myb DNA-binding domain repeat signatures (position 24–32, 96–119 amino acids).

Sequence comparison reveals that the encoded BOS1 protein (SEQ ID NO:2) has significant sequence similarity to dehydration induced myb-related proteins from the resurrection plant *Craterostigma plantagineum*, Cpm7 (NCBI #T09737), Cpm5 (NCBI#T09736) and Cpm10 (NCBI#T09735). These Cpm proteins show 76–80% identity to the BOS1 protein over a stretch of the first 152 amino acids in the amino terminus of the BOS1 protein.

Example 8

Complementation and Overexpression

The BOS1 cDNA (SEQ ID NO:1) was cloned into a binary vector and transformed into bos1 and Col-0 wild type plants. Transgenic bos1 plants carrying the UBQ3::BOS1cDNA were assayed for the *Botrytis* susceptibility phenotype. Preliminary results show that these plants are comparable to non-transgenic wild type plants in their level of *Botrytis* resistance (FIG. 7). Future testes will further evaluate disease and abiotic stress tolerance in UBQ3::BOS1 lines generated in bos1 and wild type backgrounds. Data on diseases and abiotic stress tolerance of plants with ectopic expression of the BOS1 gene will determine the utility of the BOS1 gene for plant improvement to diseases and stress tolerance.

Example 8

Construction of Binary Promoter::Reporter Plasmids

The entry vectors containing promoters of interest (the DNA sequence 5' of the initiation codon for the gene of interest) and resulting from recombination in a BP reaction between a PCR product using the promoter of interest as template and pDONRneo are used to construct a binary promoter::reporter plasmid for *Arabidopsis* transformation. The regulatory/promoter sequence is fused to the GUS reporter gene (Jefferson et al, 1987, EMBO J 6: 3901–3907) by recombination using GATEWAY™ Technology according to manufacturers protocol as described in the Instruction Manual (GATEWAY™ Cloning Technology, GIBCO BRL, Rockville, Md.). Briefly, according to this protocol the promoter fragment in the entry vector is recombined via the LR reaction with a binary *Agrobacterium* destination vector containing the GUS coding region with intron that has an attR site 5' to the GUS reporter (pNOV2374). The orientation of the inserted fragment is maintained by the att sequences and the final construct is verified by sequencing.

The construct is then transformed into *Agrobacterium tumefaciens* strains by electroporation.

pNOV2374 is a binary vector with VS1 origin of replication, a copy of the *Agrobacterium* virG gene in the backbone and a Basta resistance selectable marker cassette between the left and right border sequences of the T-DNA. The Basta selectable marker cassette comprises the *Agrobacterium tumefaciens* manopine synthase promoter (AtMas, Barker, et al, Plant Mol. Biol. 2, 335–350 (1983)) operably linked to the gene encoding Basta resistance (denoted here as "BAR", phosphinothricin acetyl transferase, White et al, Nucl Acids Res 18: 1062 (1990)) and the 35S terminator. The AtMas promoter, BAR coding sequence and 35S terminator are located at nt 4211 to 4679, nt 4680 to 5228, nt 5263 to 5488 respectively, of pNOV2374. The vector contains GATEWAY™ recombination components which were introduced into the binary vector backbone by ligating a blunt-ended cassette containing attR sites, ccdB and cholramphenicol resistance marker using the GATEWAY™ Vector Conversion System (LifeTechnologies). The GATEWAY™ cassette is located between nt 126 and 1818 of pNOV2374. The promoter cassettes are inserted through an LR recombination reaction whereby the DNA sequence of pNOV2374 between nt 126 and nt 1818 are removed and replaced with the promoter of interest flanked by att sequences. The recombination results in the promoter sequence fused to the GUS reporter gene with intron (GIG) sequence. The GIG gene contains the ST-LS1 intron from *Solanum tuberosum* at nt 385 to nt 576 of GUS SEQ ID NO:2 (obtained from Dr. Stanton Gelvin, Purdue University, and described in Narasimhulu, et al 1996, Plant Cell, 8: 873–886.). Shown below are the orientations of the selectable marker and promoter-reporter cassettes in the binary vector constructs.

For comparison of promoter activity an additional construct is produced with the known *Arabidopsis* ubiquitin 3 (Ubq3(At), Callis, et al., J. Biol. Chem. 265: 12486–12493 (1990)) promoter plus intron operatively linked to the GIG gene and the nos promoter. Shown below is the orientation of the selectable marker and promoter-reporter cassette in the binary vector construct.

Binary Vector Construct:
RB Ubq3(At) promoter with intron fragment+GIG gene+nos—AtMas+BAR+35S ter—LB

Example 10

*Arabidopsis* Transformation

1. Plant Preparation and Growth:

*Arabidopsis* seeds are sown on moistened Fafard Germinating Mix at a density of 9 seeds per 4" square pot, placed in a flat, covered with a plastic dome to retain moisture and moved to a growth chamber. Following germination the dome is removed and plants are grown for 3–5 weeks under short days (8 hrs light) to encourage vegetative growth and production of large plants with many flowers. Flowering is induced by providing long days (16 hrs. light) for 2–3 weeks, at which time plants are ready for dip inoculation into *Agrobacterium* to generate transgenic plants.

2. *Agrobacterium* Transformation, Culture Growth and Preparation for Plant Infiltration:

The binary promoter::reporter plasmids are introduced into *Agrobacteria* by electroporation. The binary plasmid confers spectinomycin resistance to the bacteria allowing cells containing the plasmid to be selected by growth of colonies on plates of LB+spectinomycin (50 mg/L). Presence of the correct promoter::GUS plasmid is confirmed by sequence analysis of the plasmid DNA isolated from the bacteria.

Two days prior to plant transformation 5 mL cultures of LB+spectinomycin (50 mg/L) are inoculated with the *Agrobacterium* strain containing the binary promoter::GUS plasmid and incubated at 30° C. for ~24 hours. Each 5 mL culture is then transferred to 500 mL of LB+spectinomycin (50 mg/L) and incubated for ~24 hours at 30° C. Each 500 mL culture is transferred to a centrifuge bottle and centrifuged at 5000 rpm for 10 minutes in a Sorvall Centrifuge. The supernatant is removed and the pelleted *Agrobacterium* cells are retained. The *Agrobacterium* cells are resuspended in 500 mL of modified Infiltration Media (IM+MOD: 50 g/L sucrose, 10 mM MgCl, 10 uM benzylaminopurine) to which 50 ul of Silwet L-77 (Dupont) has been added.

3. Plant Transformation by Dip Infiltration:

Resuspended cells are poured into 1 L tri-pour beakers. Flowering plants are inverted into the culture, making sure all inflorescences are covered with the bacteria. The beakers are gently agitated for 30 seconds, keeping all inflorescence tissue submerged. Plants are returned to growth chamber following dip inoculation of the *Agrobacterium*. A second dip may be performed 5 days later to increase transformation frequency. Seeds are harvested ~4 to 6 weeks after transformation.

4. Selection of Transgenic *Arabidopsis*:

Seeds from transformed *Arabidopsis* plants are sown on moistened Fafard Germinating Mix in a flat, covered with a dome to retain moisture and placed in a growth chamber. Following germination seedlings are sprayed with the herbicide BASTA. Transgenic plants are BASTA resistant due to the presence of the BAR gene in the binary promoter::GUS plasmid.

Example 11

Reporter Gene Assays

Promoter activity is evaluated qualitatively and quantitatively using histochemical and florescence assays for expression of the β-glucuronidase (GUS) enzyme.

1. Histochemical β-glucuronidase (GUS) Assay

For qualitative evaluation of promoter activity, various *Arabidopsis* tissues and organs are used in GUS histochemical assays. Either whole organs or pieces of tissue are dipped into GUS staining solution. GUS staining solution contains 1 mM 5-bromo4-chloro-3-indoly I glucuronide (X-Gluc, Duchefa, 20 mM stock in DMSO), 100 mM Na-phosphate buffer pH 7.0, 10 mM EDTA pH 8.0, and 0.1% Triton X100. Tissue samples are incubated at 37° C. for 1–16 hours. If necessary samples can be cleared with several washes of 70% EtOH to remove chlorophyll. Following staining tissues are viewed under a light microscope to evaluate the blue staining showing the GUS expression pattern.

2. β-glucuronidase (GUS) Florescence Assay

For quantitative analysis of promoter activity in various *Arabidopsis* tissues and organs, GUS expression is measured florometrically. Tissue samples are harvested and ground in ice cold GUS extraction buffer (50 mM Na2HPO4 pH 7.0, 5 mM DTT, 1 mM Na2EDTA, 0.1% TritonX100, 0.1% sarcosyl). Ground samples are spun in a microfuge at 10,000 rpm for 15 minutes at 4° C. Following centrifugation the supernatant is removed for GUS assay and for protein concentration determination.

To measure GUS activity the plant extract is assayed in GUS assay buffer (50 mM Na2HPO4 pH 7.0, 5 mM DTT, 1 mM Na2EDTA, 0.1% TritonX100, 0.1% sarcosyl, 1 mM 4-Methylumbelliferyl-beta-D-glucuronic acid dihydrate (MUG)), prewarmed to 37° C. Reactions are incubated and 100 uL aliquots are removed at 10 minute intervals for 30 minutes to stop the reaction by adding to tubes containing 900 uL of 2% Na2CO3. The stopped reactions are then read on a Tecan Spectroflourometer at 365 nm excitation and 455 emission wavelengths. Protein concentrations are determined using the BCA assay following manufacturers protocol. GUS activity is expressed as relative florometric units (RFU)/mg protein.

REFERENCES

Iturriaga G., Leyns L., Villegas A., Gharaibeh R (1996). "A family of novel myb-related genes from the resurrection plant Craterostigma plantagineum are specifically expresses in callus and roots in response to ABA or dessication", Plant Molecular Biology 32: 707–716.

What is claimed is:

1. An isolated promoter comprising the nucleotide sequence of SEQ ID NO: 4.

2. The isolated promoter according to claim 1, wherein said promoter controls abiotic stress responsive expression of an operably linked coding nucleotide sequence.

3. An expression cassette comprising the isolated promoter according to claim 1.

4. A recombinant vector comprising the expression cassette according to claim 3.

5. A host cell stably transformed with the expression cassette of claim 3.

6. The host cell of claim 5, wherein said host cell is a plant cell.

7. A plant comprising the plant cell of claim 6.

8. The plant of claim 7, wherein said plant is selected from the group consisting of maize, wheat, sorghum, rye, oats, turf grass, rice, barley, soybean, cotton, tobacco, sugar beet and oilseed rape.

* * * * *

SEQUENCE LISTING

```
<160> NUMBER OF SEQ ID NOS: 14

<210> SEQ ID NO 1
<211> LENGTH: 1244
<212> TYPE: DNA
<213> ORGANISM: Arabidopsis thaliana

<400> SEQUENCE: 1
aaaaactcat cctatctcta tctacacata actccaaaaa acaaacaaat tttctctctc      60
tatctctctt cgcaaaacaa catagaaaaa aagtagaaag tctcaatctt tttgctgaac    120
aatcttgttg tggtctcttc tgtgtatatc aatggatgaa aaaggaagaa gcttgaagaa    180
caacaacatg gaagacgaga tggacctaaa gagaggtccg tggactgctg aagaagattt    240
```

-continued

```
taagctcatg aattacattg ctactaatgg agaaggtcgc tggaactctc tttctcgttg    300
cgccggcctc caacgcaccg gtaaaagctg tagactaagg tggttaaact atctccgccc    360
tgacgtccgc cgtggaaaca ttacacttga gaacaactc ttgatcctcg aacttcattc     420
ccgttgggga aatagatggt caaaaatcgc acaatattta ccgggaagaa cggacaacga    480
gatcaagaac tactggagga cgcgggtgca aaagcatgcg aaacagttga atgtgatgt     540
gaatagccaa caattcaaag acacaatgaa gtacttgtgg atgcctcgac tagtcgagag    600
gattcagtca gcctcggcct catccgcagc agcagccacc accacaacca ccaccaccac    660
aggatcagcc ggcacgtcat cttgcatcac aacctctaac aatcaattca tgaattacga    720
ctacaacaac aacaacatgg gacaacagtt tggtgtaatg agcaacaatg attatatcac    780
gcctgaaaat tccagcgtgg cagtgtctcc ggcgtcagac ttaacggagt actacagcgc    840
tccaaaccct aacccggaat actattcggg tcaaatgggg aatagttatt atccagatca    900
gaatttagtg agttcacaat tattaccgga taattatttc gactatagtg gattattaga    960
cgaagatcta acggctttgc aagagcagag taacctcagc tggtttgaaa acattaatgg   1020
gggctgcttc ttcttcagac agtttatgga cattggagaa actgatgaag aattctggtt   1080
cttacagcag caacaacagt tcaacaataa tggtagcttc tgaagttaga aaaaaaaat    1140
agraatcgtt ttaagttaaa ttatacccta tagtatacgt gtgaaaggaa tttgttgtaa   1200
gggaaaaaaa aaaaaaaaaa aaaaaaaaa aaaaaaaaa aaaa                     1244
```

<210> SEQ ID NO 2
<211> LENGTH: 323
<212> TYPE: PRT
<213> ORGANISM: Arabidopsis thaliana

<400> SEQUENCE: 2

```
Met Asp Glu Lys Gly Arg Ser Leu Lys Asn Asn Asn Met Glu Asp Glu
1               5                   10                  15

Met Asp Leu Lys Arg Gly Pro Trp Thr Ala Glu Glu Asp Phe Lys Leu
            20                  25                  30

Met Asn Tyr Ile Ala Thr Asn Gly Glu Gly Arg Trp Asn Ser Leu Ser
        35                  40                  45

Arg Cys Ala Gly Leu Gln Arg Thr Gly Lys Ser Cys Arg Leu Arg Trp
    50                  55                  60

Leu Asn Tyr Leu Arg Pro Asp Val Arg Arg Gly Asn Ile Thr Leu Glu
65                  70                  75                  80

Glu Gln Leu Leu Ile Leu Glu Leu His Ser Arg Trp Gly Asn Arg Trp
                85                  90                  95

Ser Lys Ile Ala Gln Tyr Leu Pro Gly Arg Thr Asp Asn Glu Ile Lys
            100                 105                 110

Asn Tyr Trp Arg Thr Arg Val Gln Lys His Ala Lys Gln Leu Lys Cys
        115                 120                 125

Asp Val Asn Ser Gln Gln Phe Lys Asp Thr Met Lys Tyr Leu Trp Met
    130                 135                 140

Pro Arg Leu Val Glu Arg Ile Gln Ser Ala Ser Ala Ser Ser Ala Ala
145                 150                 155                 160

Ala Ala Thr Thr Thr Thr Thr Thr Thr Gly Ser Ala Gly Thr Ser
                165                 170                 175

Ser Cys Ile Thr Thr Ser Asn Asn Gln Phe Met Asn Tyr Asp Tyr Asn
            180                 185                 190
```

```
Asn Asn Asn Met Gly Gln Gln Phe Gly Val Met Ser Asn Asn Asp Tyr
            195                 200                 205

Ile Thr Pro Glu Asn Ser Ser Val Ala Val Ser Pro Ala Ser Asp Leu
    210                 215                 220

Thr Glu Tyr Tyr Ser Ala Pro Asn Pro Asn Pro Glu Tyr Tyr Ser Gly
225                 230                 235                 240

Gln Met Gly Asn Ser Tyr Tyr Pro Asp Gln Asn Leu Val Ser Ser Gln
                245                 250                 255

Leu Leu Pro Asp Asn Tyr Phe Asp Tyr Ser Gly Leu Leu Asp Glu Asp
            260                 265                 270

Leu Thr Ala Leu Gln Glu Gln Ser Asn Leu Ser Trp Phe Glu Asn Ile
        275                 280                 285

Asn Gly Gly Cys Phe Phe Phe Arg Gln Phe Met Asp Ile Gly Glu Thr
290                 295                 300

Asp Glu Glu Phe Trp Phe Leu Gln Gln Gln Gln Gln Phe Asn Asn Asn
305                 310                 315                 320

Gly Ser Phe
```

<210> SEQ ID NO 3
<211> LENGTH: 3632
<212> TYPE: DNA
<213> ORGANISM: Arabidopsis thaliana

<400> SEQUENCE: 3

```
attattatag cacaaagttt tcaatagaaa tcagaaaacg gaaacagagt tattttatgc      60
acggagatgg aaagtcagcg ggtcaactat taaaactcag tgcttaatta agtggtaagt     120
gataattaac tctttactaa attattcctg ctggagtcct ttaaggcttt aactgatatt     180
ttatctggac ggcatctttt tctgcttata gacttctagt attaactctt catctggttc     240
agtttttaat tttaacccct acaattttca atagactata ttaattctta tttatagatt     300
ttcaaatatt tttgtatttt tcttaattgg tttaggttta actaagacct ctttaattct     360
tgatataaag agtattaact aaagacgaga gtgttttttt ttttttttttt ttgcaccaaa    420
ccaagtaaca agaggaaact aaaaactctt tgaagcatg tcgatcctaa attaagtttt      480
ttatttagtg ctcttttatc aacgtgacag aatattaacc acaataacat ctaattttag     540
tatttctgta tatgattttt tttttttttt ttttttttt ttttttttga aagttactac      600
tctcaccaca tgggaaaaaa atagttttac caaaatctga ataacaaaa cgaagtaagt      660
actaacaata ccaccgaaga tttattgctg gtcgcgtttt ttattactaa atttgatgtt     720
ttatgtttac actttgactg tttgccaacc aaaaaaaaaa aaaaaaaaat gtttacactt     780
tgactatata tttatcataa ctctaatttt aatttaaata ttttgaaatt attaatcatt     840
attatttatt tgtaattaga tatacgaaaa tattttatac attcatatca tatagtctta     900
accttcacgc acataaaatt atagtttttg tttgtatgtg cgtatagtta aaaatgaagt     960
aggctcaaaa ctatgatttt tttttttttt tttaaatgtg aaatattcca ttgatgaatt   1020
aaattcataa ttttgaaatt tatgtaatta tatggatacg gaaggctata atgaaatttg   1080
aatgcaaaga ctcacttccc ctaagagaat aataattgtt cagccaagtg gactactcgt   1140
attcgatagt ttttttttca ccttcacgaa ttctaaaact ttgaagagct ataaacaga    1200
atttaagagt acaaaattat aaaaaaaatt aaatcaataa acatacagtt cctgctgcca   1260
aaaaataaaa ataaaaaata aacatacagt tcctatatta cggctgtcta ttcccttcat   1320
cgcacatgtt ccaaataatt ttaaaaaata aaagaaaaaa ttgaaaacta tcttcttttt   1380
```

-continued

```
tcttctataa aacccacaac ttctcttttt cttgtgcatt caaaactcat cctatctcta      1440
tctacacata actccaaaaa acaaacaaat tttctctctc tatctctctt cgcaaaacaa      1500
catagaaaaa aagtagaaag tctcaatctt tttgctgaac aatcttgttg tggtctcttc      1560
tgtgtatatc aatggatgaa aaaggaagaa gcttgaagaa caacaacatg gaagacgaga      1620
tggacctaaa gagaggtccg tggactgctg aagaagattt taagctcatg aattacattg      1680
ctactaatgg agaaggtcgc tggaactctc tttctcgttg cgccggtatg atatatattt      1740
tcatatacag ataatatagt tgtatatatc tattttccac ttccatgagc atcttttaag      1800
cataaagagc caaagaacaa gtcgcataac ataattgatt tattgctttt tgttcaatcc      1860
ttttcatgtt tcaatcacca tgtgtgattt gtgttttttt ttttctttta aattgcccaa      1920
cctttactat ttttaaagat agttttagga aaaattatt attcgaaaat ggtttctttc       1980
cctatatgca tatatgaaaa gacccttcat aggtatgaat caaaaagtgc atacctctca      2040
tgttttctct ttctcgtctt cttcttattt ctaaatataa tttccttcca ataaataaag      2100
tattgatgat ttgagtgaga tcttttggta atggattcaa ttattaacca tctcaaattt      2160
gaataaaata tccaaatttg gttattaaat gggtgaaaaa aagaagaact aatgcgaatt      2220
aatgatcatc atctataagg gaagagcact aactcaatgg gagaaagctt gctgaagaaa      2280
aagaccettt aggacaattt gcatcataat acggtccatt ttatttcatt ggggaatttg      2340
atataacttt aacgaaaatg aaacaaatat tataatgagt ttcttccgta taaaatcatc      2400
atactatacg tagacatgac cgaccggtaa attaatcctc atattatctt ttaccaatga      2460
aacaggcctc caacgcaccg gtaaaagctg tagactaagg tggttaaact atctccgccc      2520
tgacgtccgc cgtggaaaca ttcacttgaa gaacaactc ttgatcctcg aacttcattc        2580
ccgttgggga ataggtatg ctaaattaaa ataaataaaa cagtataaca ccttttccaa        2640
ctaaattata caatatgtag ttgatgagtt tatttaaatg aattaaatct ggttttacat      2700
aaaattatgc atcaaacata taataagatt ttttttgtga attggaaata aaataacatc      2760
ataactatt  taaaatggag aaaataacaa attatgtcga tgttgatgga tgaaaagaga      2820
ttaaatgtat gatactgaga tatactaatg aataataatg ttatagacgc caagaaaata      2880
agaatttgat tatcactact attagtttag aaccgttaat ttatatcttg ttattttgat      2940
gtagatggtc aaaaatcgca caatatttac cgggaagaac ggacaacgag atcaagaact      3000
actggaggac gcgggtgcaa aagcatgcga aacagttgaa atgtgatgtg aatagccaac      3060
aattcaaaga cacaatgaag tacttgtgga tgcctcgact agtcgagagg attcagtcag      3120
cctcggcctc atccgcagca gcagccacca ccacaaccac caccaccaca ggatcagccg      3180
gcacgtcatc ttgcatcaca acctctaaca atcaattcat gaattacgac tacaacaaca      3240
acaacatggg acaacagttt ggtgtaatga gcaacaatga ttatatcacg cctgaaaatt      3300
ccagcgtggc agtgtctccg gcgtcagact taacggagta ctacagcgct ccaaacccta      3360
acccggaata ctattcgggt caaatgggga atagttatta tccagatcag aatttagtga      3420
gttcacaatt attaccggat aattatttcg actatagtgg attattagac gaagatctaa      3480
cggctatgca agagcagagt aacctcagct ggtttgaaaa cattaatggt gctgcttctt      3540
cttcagacag tttatggaac attggagaaa ctgatgaaga attctggttc ttacagcagc      3600
aacaacagtt caacaataat ggtagcttct ga                                    3632
```

<210> SEQ ID NO 4

<211> LENGTH: 1551
<212> TYPE: DNA
<213> ORGANISM: Arabidopsis thaliana

<400> SEQUENCE: 4

| | | | | | |
|---|---|---|---|---|---|
| tcaatagaaa | tcagaaaacg | gaaacagagt | tattttatgc | acggagatgg | aaagtcagcg | 60 |
| ggtcaactat | taaaactcag | tgcttaatta | agtggtaagt | gataattaac | tctttactaa | 120 |
| attattcctg | ctggagtcct | ttaaggcttt | aactgatatt | ttatctggac | ggcatctttt | 180 |
| tctgcttata | gacttctagt | attaactctt | catctggttc | agtttttaat | ttttaaccct | 240 |
| acaattttca | atagactata | ttaattctta | tttatagatt | ttcaaatatt | tttgtatttt | 300 |
| tcttaattgg | tttaggttta | actaagacct | ctttaattct | tgatataaag | agtattaact | 360 |
| aaagacgaga | gtgttttttt | tttttttttt | ttgcaccaaa | ccaagtaaca | agaggaaact | 420 |
| aaaaactctt | tgaagcatg | tcgatcctaa | attaagtttt | ttatttagtg | ctcttttatc | 480 |
| aacgtgacag | aatattaacc | acaataacat | ctaattttag | tatttctgta | tatgattttt | 540 |
| tttttttttt | tttttttttt | tttttttga | aagttactac | tctcaccaca | tgggaaaaaa | 600 |
| atagttttac | caaaatctga | ataacaaaa | cgaagtaagt | actaacaata | ccaccgaaga | 660 |
| tttattgctg | gtcgcgtttt | ttattactaa | atttgatgtt | ttatgtttac | actttgactg | 720 |
| tttgccaacc | aaaaaaaaaa | aaaaaaaaat | gtttacactt | tgactatata | tttatcataa | 780 |
| ctctaatttt | aatttaaata | ttttgaaatt | attaatcatt | attatttatt | tgtaattaga | 840 |
| tatacgaaaa | tattttatac | attcatatca | tatagtctta | accttcacgc | acataaaatt | 900 |
| atagttttg | tttgtatgtg | cgtatagtta | aaaatgaagt | aggctcaaaa | ctatgatttt | 960 |
| ttttattttt | tttaaatgtg | aaatattcca | ttgatgaatt | aaattcataa | ttttgaaatt | 1020 |
| tatgtaatta | tatggatacg | gaaggctata | atgaaatttg | aatgcaaaga | ctcacttccc | 1080 |
| ctaagagaat | aataattgtt | cagccaagtg | gactactcgt | attcgatagt | ttttttttca | 1140 |
| ccttcacgaa | ttctaaaact | ttgaagagct | tataaacaga | atttaagagt | acaaaattat | 1200 |
| aaaaaaaatt | aaatcaataa | acatacagtt | cctgctgcca | aaaataaaa | ataaaaaata | 1260 |
| aacatacagt | tcctatatta | cggctgtcta | ttcccttcat | cgcacatgtt | ccaaataatt | 1320 |
| ttaaaaaata | aaaagaaaaa | ttgaaaacta | tcttcttttt | tcttctataa | aacccacaac | 1380 |
| ttctcttttt | cttgtgcatt | caaaactcat | cctatctcta | tctacacata | actccaaaaa | 1440 |
| acaaacaaat | tttctctctc | tatctctctt | cgcaaaacaa | catagaaaaa | aagtagaaag | 1500 |
| tctcaatctt | tttgctgaac | aatcttgttg | tggtctcttc | tgtgtatatc | a | 1551 |

<210> SEQ ID NO 5
<211> LENGTH: 27
<212> TYPE: DNA
<213> ORGANISM: Artificial sequence
<220> FEATURE:
<223> OTHER INFORMATION: primer

<400> SEQUENCE: 5
gacgtccgcc gtggaaacat tacactt                27

<210> SEQ ID NO 6
<211> LENGTH: 27
<212> TYPE: DNA
<213> ORGANISM: artificial sequence
<220> FEATURE:
<223> OTHER INFORMATION: primer

<400> SEQUENCE: 6

```
ggaagaacgg acaacgagat caagaac                                27

<210> SEQ ID NO 7
<211> LENGTH: 29
<212> TYPE: DNA
<213> ORGANISM: artificial sequence
<220> FEATURE:
<223> OTHER INFORMATION: primer

<400> SEQUENCE: 7
tagtactccg ttaagtctga cgccggaga                              29

<210> SEQ ID NO 8
<211> LENGTH: 24
<212> TYPE: DNA
<213> ORGANISM: artificial sequence
<220> FEATURE:
<223> OTHER INFORMATION: primer

<400> SEQUENCE: 8
atgcaagatg acgtgccggc tgat                                   24

<210> SEQ ID NO 9
<211> LENGTH: 27
<212> TYPE: DNA
<213> ORGANISM: Artificial sequence
<220> FEATURE:
<223> OTHER INFORMATION: primer

<400> SEQUENCE: 9
atggatgaaa aaggaagaag cttgaag                                27

<210> SEQ ID NO 10
<211> LENGTH: 27
<212> TYPE: DNA
<213> ORGANISM: Artificial sequence
<220> FEATURE:
<223> OTHER INFORMATION: primer

<400> SEQUENCE: 10
tcagaagcta ccattattgt tgaactg                                27

<210> SEQ ID NO 11
<211> LENGTH: 24
<212> TYPE: DNA
<213> ORGANISM: Artificial sequence
<220> FEATURE:
<223> OTHER INFORMATION: primer

<400> SEQUENCE: 11
tgcaccaaac caagtaacaa gagg                                   24

<210> SEQ ID NO 12
<211> LENGTH: 30
<212> TYPE: DNA
<213> ORGANISM: Artificial sequence
<220> FEATURE:
<223> OTHER INFORMATION: primer

<400> SEQUENCE: 12
ctagctagct cagaagctac cattattgtt                             30

<210> SEQ ID NO 13
<211> LENGTH: 20
<212> TYPE: DNA
```

```
<213> ORGANISM: Artificial sequence
<220> FEATURE:
<223> OTHER INFORMATION: primer

<400> SEQUENCE: 13
tcaatagaaa tcagaaaacg                                              20

<210> SEQ ID NO 14
<211> LENGTH: 21
<212> TYPE: DNA
<213> ORGANISM: Artificial sequence
<220> FEATURE:
<223> OTHER INFORMATION: primer

<400> SEQUENCE: 14
tgatatacac agaagagacc a                                            21
```